United States Patent
Du et al.

(10) Patent No.: US 10,857,243 B2
(45) Date of Patent: Dec. 8, 2020

(54) ENZYMATICALLY RESPONSIVE MAGNETIC PARTICLES AND THEIR USE

(71) Applicant: BRANDEIS UNIVERSITY, Waltham, MA (US)

(72) Inventors: Xuewen Du, Waltham, MA (US); Jie Zhou, Waltham, MA (US); Bing Xu, Newton, MA (US)

(73) Assignee: BRANDEIS UNIVERSITY, Waltham, MA (US)

(*) Notice: Subject to any disclaimer, the term of this patent is extended or adjusted under 35 U.S.C. 154(b) by 436 days.

(21) Appl. No.: 15/303,117

(22) PCT Filed: Apr. 9, 2015

(86) PCT No.: PCT/US2015/025137
§ 371 (c)(1),
(2) Date: Oct. 10, 2016

(87) PCT Pub. No.: WO2015/157530
PCT Pub. Date: Oct. 15, 2015

(65) Prior Publication Data
US 2017/0119910 A1 May 4, 2017

Related U.S. Application Data

(60) Provisional application No. 61/977,484, filed on Apr. 9, 2014, provisional application No. 62/063,773, filed on Oct. 14, 2014.

(51) Int. Cl.
*A61K 9/00* (2006.01)
*A61K 49/18* (2006.01)
(Continued)

(52) U.S. Cl.
CPC .......... *A61K 49/1866* (2013.01); *A61K 38/08* (2013.01); *A61K 41/0052* (2013.01);
(Continued)

(58) Field of Classification Search
CPC ................................................. A61K 49/1866
See application file for complete search history.

(56) References Cited

U.S. PATENT DOCUMENTS

| 6,887,856 B1 | 5/2005 | Greenberger |
| 2002/0168684 A1* | 11/2002 | Comb ................ C07K 16/00 435/7.1 |

(Continued)

FOREIGN PATENT DOCUMENTS

| WO | 2002/010442 A1 | 2/2002 |
| WO | 2003/102544 A2 | 12/2003 |

(Continued)

OTHER PUBLICATIONS

Wang, Phosphorylation of Osteopontin is Required for Inhibition of Calcium Oxalate Crystallization, J. Phys. Chem. B, 2008, 112(30), 9151-9157.*

(Continued)

*Primary Examiner* — Paul W Dickinson
(74) *Attorney, Agent, or Firm* — Troutman Pepper Hamilton Sanders LLP (Rochester)

(57) ABSTRACT

The invention relates to an enzymatically responsive product that includes an amino acid residue conjugated to a magnetic particle, wherein the amino acid residue is phosphorylated or sulfated or comprises an ester-moiety linked via peptide bond. Compositions containing the enzymatically responsive product, and the use thereof for separating distinct types of mammalian cells (e.g., cancer cells from normal cells), for treating a cancerous condition, and imaging cancer cells are also disclosed.

15 Claims, 10 Drawing Sheets

Specification includes a Sequence Listing.

(51) Int. Cl.
| | |
|---|---|
| G01N 33/543 | (2006.01) |
| G01N 33/574 | (2006.01) |
| C12Q 1/42 | (2006.01) |
| A61K 47/52 | (2017.01) |
| A61K 47/69 | (2017.01) |
| A61K 47/64 | (2017.01) |
| A61K 38/08 | (2019.01) |
| A61K 41/00 | (2020.01) |
| A61K 45/06 | (2006.01) |
| B82Y 5/00 | (2011.01) |
| A61B 17/00 | (2006.01) |

(52) U.S. Cl.
CPC .............. *A61K 45/06* (2013.01); *A61K 47/52* (2017.08); *A61K 47/64* (2017.08); *A61K 47/6923* (2017.08); *A61K 47/6929* (2017.08); *C12Q 1/42* (2013.01); *G01N 33/54326* (2013.01); *G01N 33/574* (2013.01); *G01N 33/57492* (2013.01); *A61B 2017/00345* (2013.01); *B82Y 5/00* (2013.01); *G01N 2333/916* (2013.01); *G01N 2440/14* (2013.01); *G01N 2440/30* (2013.01)

(56) References Cited

U.S. PATENT DOCUMENTS

| | | | |
|---|---|---|---|
| 2007/0122429 | A1 | 5/2007 | Kay et al. |
| 2007/0264665 | A1 | 11/2007 | Akhavan-Tafti |
| 2009/0136594 | A1 | 5/2009 | McLeroy et al. |
| 2011/0182815 | A1 | 7/2011 | Daich |
| 2012/0142616 | A1 | 6/2012 | Gao et al. |
| 2013/0023024 | A1 | 1/2013 | Ying et al. |
| 2014/0148410 | A1 | 5/2014 | Xu |

FOREIGN PATENT DOCUMENTS

| | | |
|---|---|---|
| WO | 2010/151644 A2 | 12/2010 |
| WO | 2012/166705 A2 | 12/2012 |
| WO | 2012/166706 A2 | 12/2012 |
| WO | 2014/138367 A1 | 9/2014 |

OTHER PUBLICATIONS

International Search Report and Written Opinion for corresponding Application No. PCT/US2015/025137 (dated Sep. 30, 2015).
Yin et al., "SERS-Active Nanoparticles for Sensitive and Selective Detection of Cadmium Ion (Cd2+)," Chem. Mater. 23(21):4756-4764 (2011).
Manka et al., "Structural Insights into Triple-Hellical Collagen Cleavage by Matrix Metloproeinase 1," Proc. Nat. Acad. Sci. U.S.A. 109(31):12461-12466 (2012).
Zhou et al., "A Magnetic Bead-Based Protein Kinase Assay with Dual Detection Techniques," Anal. Biochem. 408(1):5-11 (2011).
Freitas-Mesquita et al., "Biochemical Properties and Possible Roles of Ectophosphatase Activities in Fungi," Int. J. Mol. Sci. 15:2289-2304 (2014).
Liang et al., "Supramolecular Hydrogel of a D-Amino Acid Dipeptide for Controlled Drug Release in Vivo," Langmuir 25(15):8419-422 (2009).
Gao et al., "Imaging Enzyme-Triggered Self-Assembly of Small Molecules Inside Live Cells," Nat Commun. 3:1033 (2012).
Li et al., "Molecular Nanofibers of Olsalazine Confer Supramolecular Hydrogels for Reductive Release of an Anti-Inflammatory Agent," J Am Chem Soc. 132(50):17707-709 (2010).
Zhang et al., "Versatile Small Molecule Motifs for Self-Assembly in Water and Formation of Biofunctional Supramolecular Hydrogels," Langmuir. 27(2):529-37 (2011).
Li et al., "The Conjugation of Nonsteroidal Anti-Inflammatory Drugs (NSAID) to Small Peptides for Generating Multifunctional Supramolecular Nanofibers/Hydrogels," Beilstein J. Org. Chem. 9:908-917 (2013).
Li et al., "Introducing D-Amino Acid or Simple Glycoside into Small Peptides to Enable Supramolecular Hydrogelators to Resist Proteolysis," Langmuir. 28(37):13512-517 (2012).
Li et al., "'Molecular Trinity' for Soft Nanomaterials: Integrating Nucleobases, Amino Acids, and Glycosides to Construct Multifunctional Hydrogelators," Soft Matter. 8(10):2801-806 (2012).
Zhao et al., "A Novel Anisotropic Supramolecular Hydrogel with High Stability over a Wide PH Range," Langmuir. 27(4):1510-12 (2011).
Li et al., "Supramolecular Nanofibers and Hydrogels of Nucleopeptides," Angew Chem Int Ed Engl. 50(40):9365-69 (2011).
International Preliminary Report on Patentability from PCT/US2015/025137 (dated Oct. 12, 2016).

* cited by examiner

FIGS. 4A-D

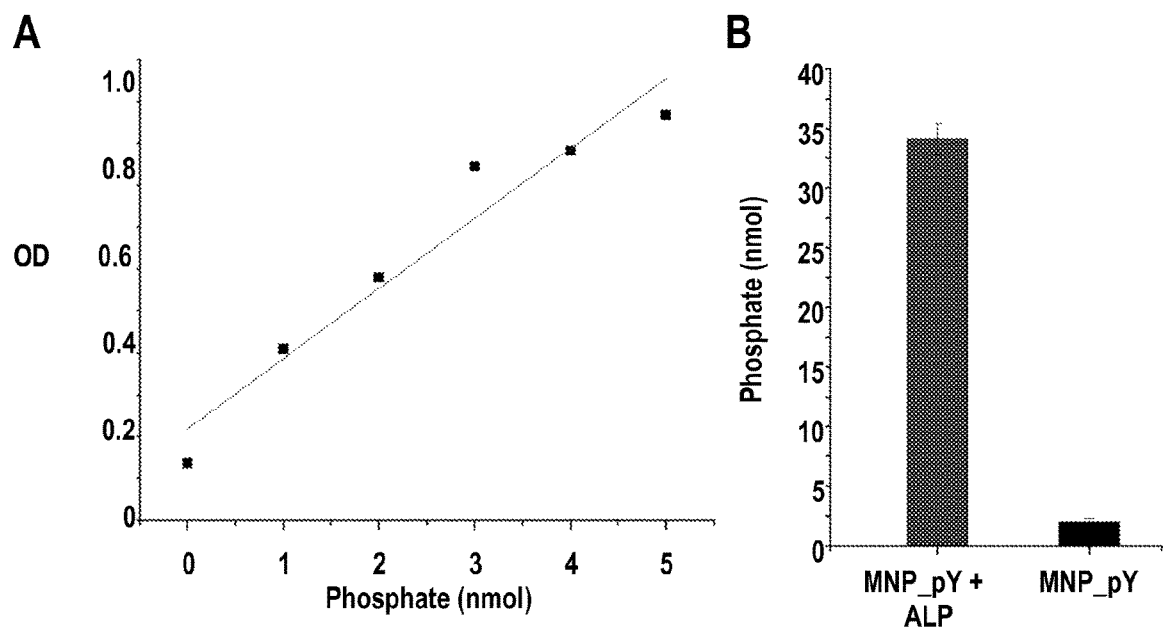
*FIGS. 7A-B*
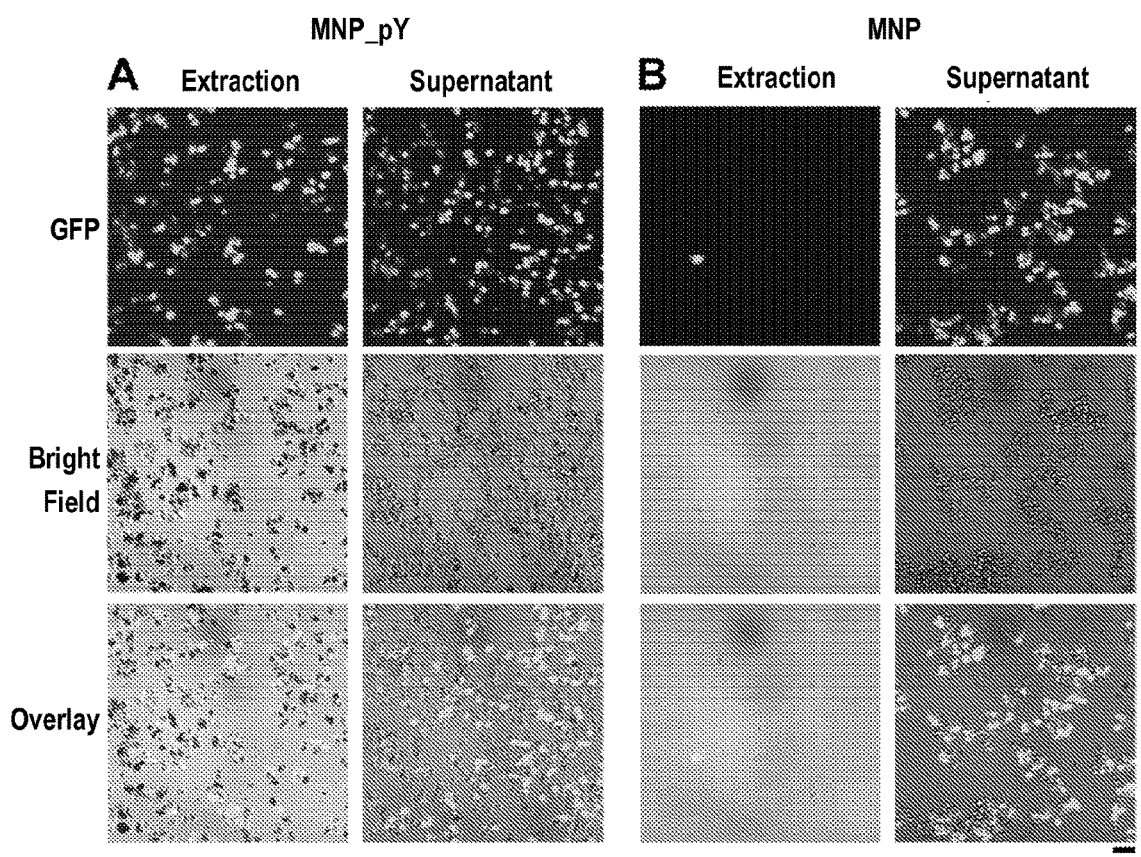
*FIGS. 8A-B*

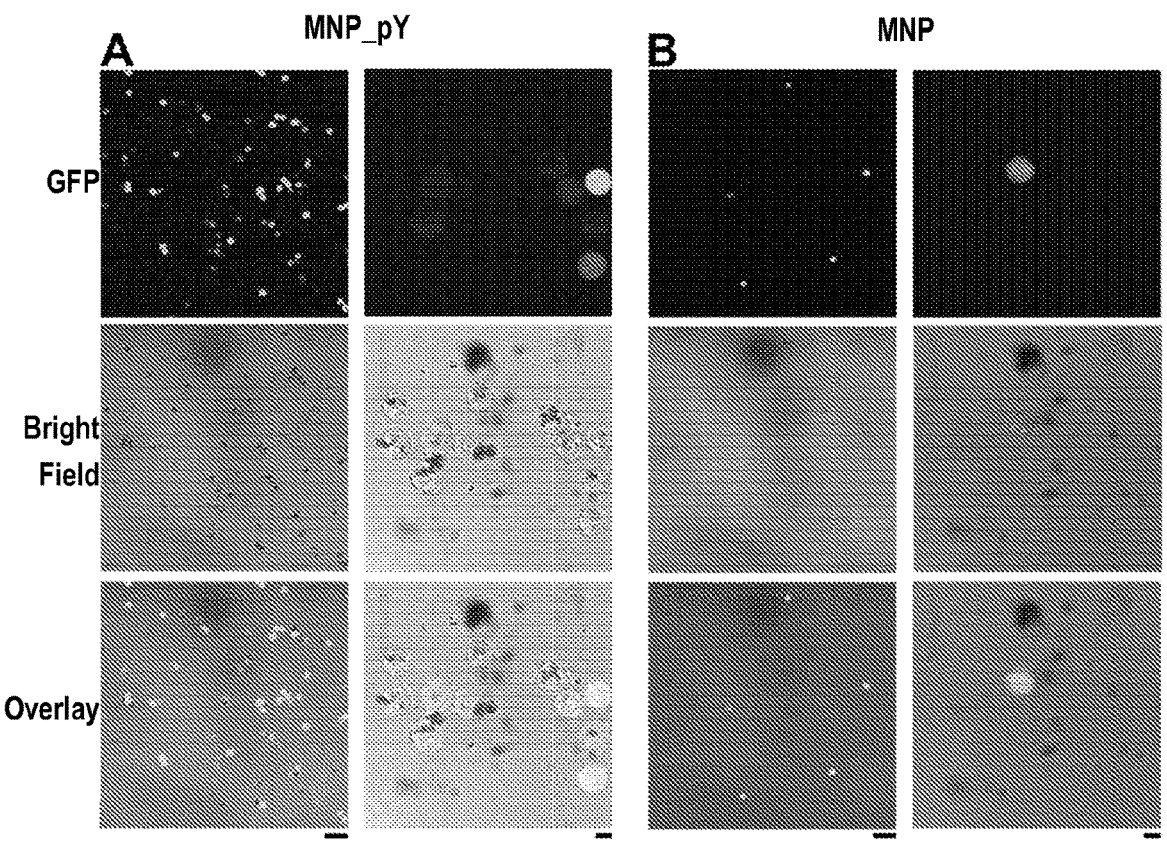
FIGS. 9A-B
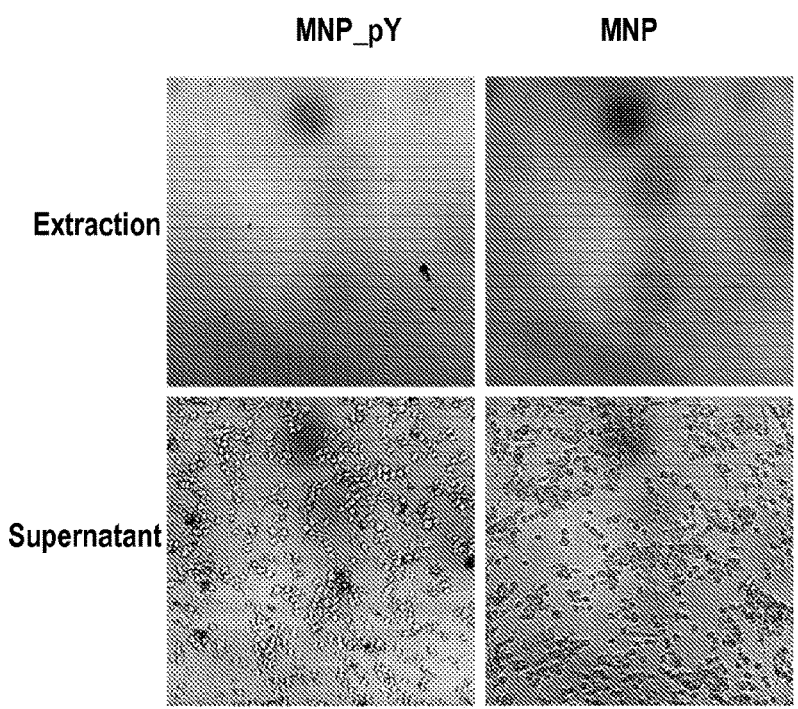
FIG. 10

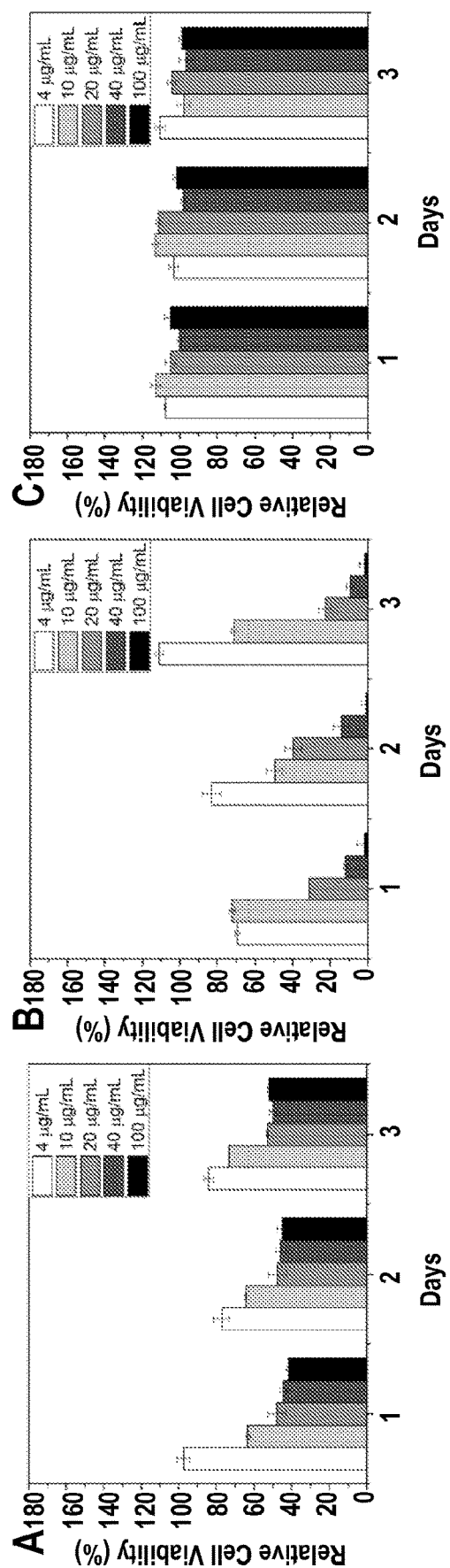
FIGS. 12A-C
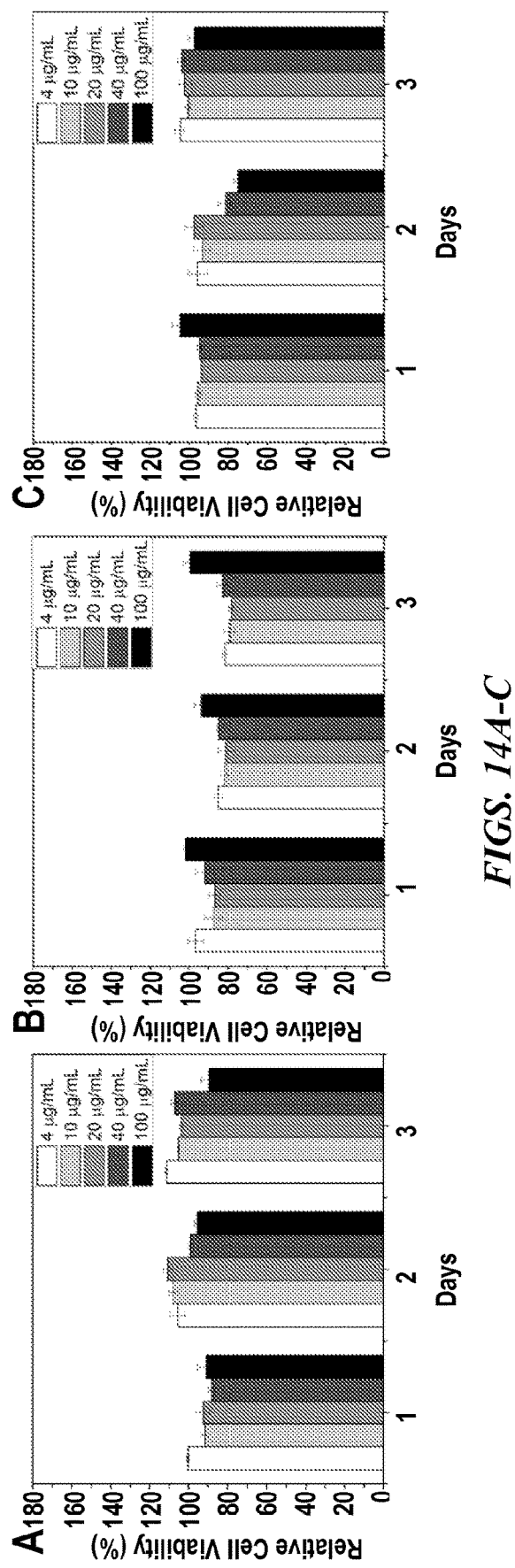
FIGS. 14A-C

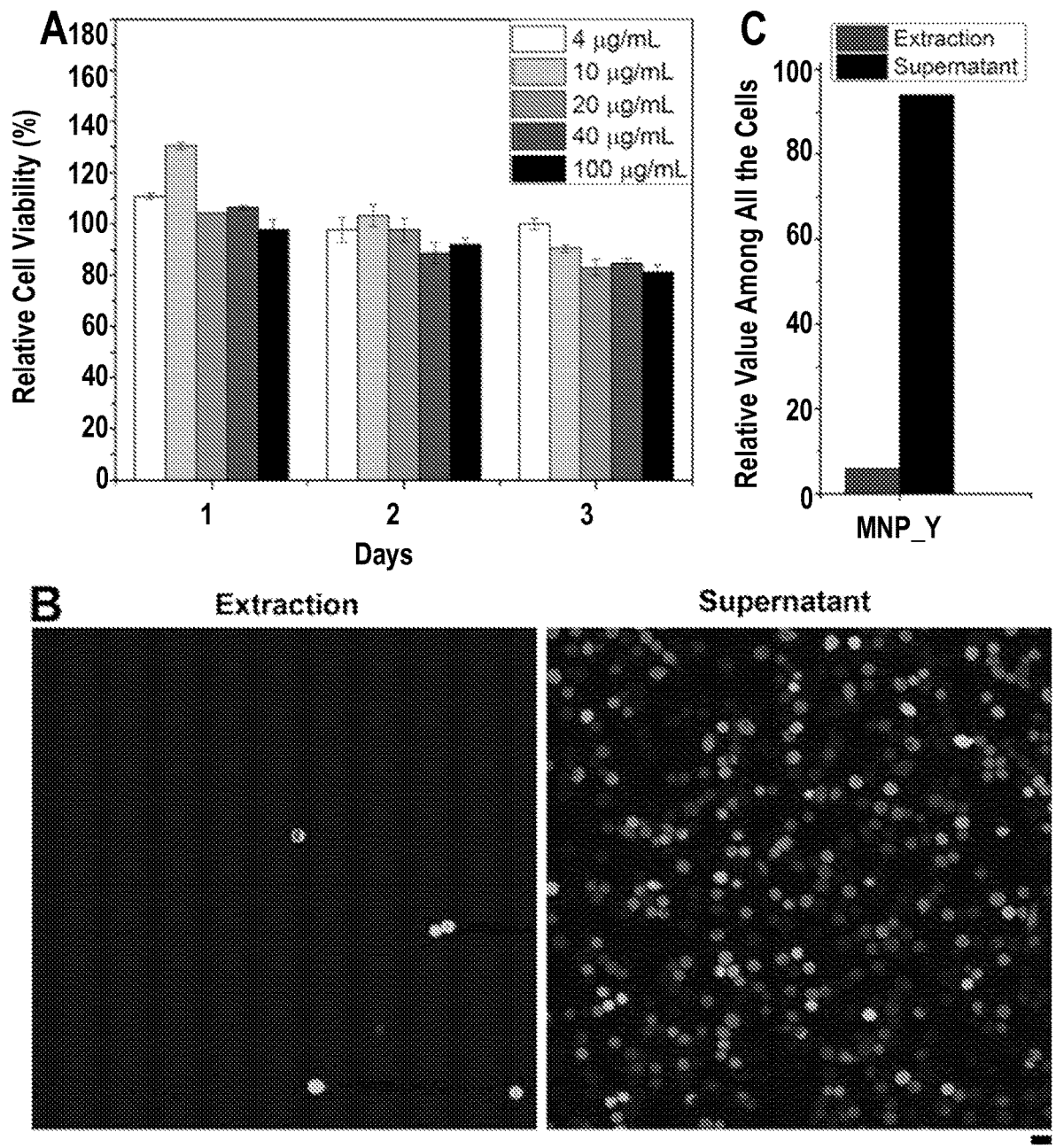
*FIGS. 15A-C*

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 1

Xaa Gly Pro Gln Gly Leu Ala Gly Gln
1               5

<210> SEQ ID NO 2
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 2

Xaa Ala Pro Ala Ala Leu Val Gly Ala
1               5

<210> SEQ ID NO 3
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
```

```
<223> OTHER INFORMATION: x is any aromatic group, aromatic amino acid,
      or hydrophobic amino acid

<400> SEQUENCE: 3

Xaa Ala Pro Ala Gly Leu Lys Ala Pro
1               5

<210> SEQ ID NO 4
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 4

Xaa Glu Pro Ala Ser Leu Arg Ala Gly
1               5

<210> SEQ ID NO 5
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 5

Xaa Gly Pro Gln Gly Leu Arg Gly Arg
1               5

<210> SEQ ID NO 6
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 6

Xaa Gly Pro Ala Gly Leu Arg Gly Pro
1               5

<210> SEQ ID NO 7
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid
```

```
<400> SEQUENCE: 7

Xaa Gly Pro Ala Gly Leu Gly Ala Ala
1               5

<210> SEQ ID NO 8
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 8

Xaa Gly Pro Lys Gly Leu Arg Gly Gly
1               5

<210> SEQ ID NO 9
<211> LENGTH: 9
<212> TYPE: PRT
<213> ORGANISM: Artificial
<220> FEATURE:
<223> OTHER INFORMATION: polypeptide with a metalloprotease cleavage
      site
<220> FEATURE:
<221> NAME/KEY: MISC_FEATURE
<222> LOCATION: (1)..(1)
<223> OTHER INFORMATION: x is any aromatic group, aromatic amino acid,
      or hydrophobic amino acid

<400> SEQUENCE: 9

Xaa Leu Pro Leu Gly Leu Val Thr Glu
1               5
```

ENZYMATICALLY RESPONSIVE MAGNETIC PARTICLES AND THEIR USE

This application is a national stage application under 35 U.S.C. § 371 of PCT Application No. PCT/US2015/025137, filed Apr. 9, 2015, which claims the benefit of U.S. Provisional Patent Application Ser. No. 61/977,484 filed Apr. 9, 2014 and U.S. Provisional Patent Application Ser. No. 62/063,773, filed Oct. 14, 2014, each of which is hereby incorporated by reference in its entirety.

This invention was made with government support under grant R01CA142746 awarded by the National Institutes of Health and under grant DMR-0820492 awarded by the National Science Foundation. The government has certain rights in the invention.

FIELD OF THE INVENTION

The present invention relates generally to the field of cancer diagnostics and therapeutics, including an enzymatically responsive product and its use for sorting cancerous and noncancerous cells, diagnosing cancerous conditions, and treating cancerous conditions.

BACKGROUND OF THE INVENTION

Cell sorting, the isolation of certain types of cells from mixed cell population of organs or tissues, has become an increasingly important sampling method that has already contributed to many advances in biology and medicine (Claros et al., *Eur. J. Biochem.* 241:779 (1996); Panyam et al., *Adv. Drug Deliver. Rev.* 55:329 (2003); Cormack et al., *Gene* 173:33 (1996)). While the capture of bacteria is relatively easy by the magnetic nanoparticles decorated by a readily accessible ligand (e.g., vancomycin) (Xing et al., *J. Am. Chem. Soc.* 124:14846 (2002); Xing et al., *Chem. Commun.* 2224 (2003); Liu et al., *Nat. Commun.* 2 (2011)), the sorting of mammalian cells requires more complicated and expensive instruments and reagents. Fluorescent activated cell sorting (FACS) (Julius et al., *Proc. Natl. Acad. Sci. U.S.A* 69:1934 (1972); Kreth et al., *Cell Immunol.* 12:396 (1974)), the most widely-used cell sorting method, uses expensive hardware and requires labeling the cells of interest by fluorescent antibodies or cellular proteins (Cormack et al., *Gene* 173:33 (1996); Orlic et al., *Nature* 410:701 (2001)). The current magnetic cell sorting still requires cell specific antibodies to be conjugated to the magnetic beads, which is a less well-defined process due to the non-specific binding of proteins to the beads. Moreover, the high cost of FACS and cell specific antibodies is rather prohibitive for the applications of cell sorting for disease diagnosis in developing regions, thus, there is an unmet need to apply chemistry for the development of inexpensive cell sorting method that will contribute to low-cost diagnostics for the developing world (Martinez et al., *Anal. Chem.* 82:3 (2010); Martinez et al., *Lab Chip* 8:2146 (2008); Sia et al., *Angew. Chem. Int. Edit.* 43:498 (2004); Kuo et al., *Lab Chip* 11:2656 (2011); Kuo et al., *Electrophoresis* 25:3796 (2004)).

The present invention overcomes these and other deficiencies in the art.

SUMMARY OF THE INVENTION

A first aspect of the invention relates to an enzymatically responsive product that includes an amino acid residue conjugated to a magnetic particle, wherein the amino acid residue is phosphorylated or sulfated or comprises an ester-moiety linked via peptide bond.

A second aspect of the invention relates to a composition that includes an aqueous carrier and a product according to the first aspect of the invention.

A third aspect of the invention relates to a method of separating distinct types of cells that includes exposing a product according to the first aspect of the invention or a composition according to the second aspect of the invention to a mixed population of cells including a first cell type that expresses an ectoenzyme that hydrolyzes the phosphate group, the sulfate group, or the ester-moiety of the product, and a second cell type that lacks an ectoenzyme that hydrolyzes the phosphate group, the sulfate group, or the ester-moiety of the product, whereby the product labels the first cell type after said exposing; and separating the labeled first cell type from the second cell type. In certain embodiments, the cells are mammalian cells, particularly cancerous and non-cancerous cells.

A fourth aspect of the invention relates to a method for treating a cancerous condition that includes administering to a subject having a cancerous condition a therapeutically effective amount of the product according to the first aspect of the invention or a composition according to the second aspect of the invention, wherein said administering is effective to cause selective adherence of the dephosphorylated, desulfated, or de-esterified product to cancer cells, whereby said selective adherence affects growth or survival of cancer cells.

In one embodiment, the selective adherence of the dephosphorylated, desulfated, or de-esterified product to cancer cells is sufficient, without more, to affect growth or survival of those cancer cells.

In another embodiment, the magnetic particle is used to implement hyperthermic treatment of the cancer cells to which the dephosphorylated, desulfated, or de-esterified product is adhered. Because the dephosphorylated, desulfated, or de-esterified product selectively adheres to cancer cells that express or secrete an ectoenzyme that hydrolyzes the phosphate group, sulfate group, or ester moiety, exposing a tumor-containing region of the subject's body to an energy source (e.g., ultrasound, laser light, near infrared light, or alternating magnetic field) suitable to cause thermal heating of the magnetic particles adhered to the cancer cells and, thus, destruction of the cancer cells.

A fifth aspect of the present invention relates to a method for imaging cancer cells. This method includes administering to a subject having a cancerous condition a product according to the first aspect of the invention or a composition according to the second aspect of the invention, wherein the administering is effective to cause the product to contact cancer cells that express a cell surface-bound phosphatase or sulfatase, secrete a phosphatase or sulfatase, or both, and cause selective adherence of the dephosphorylated, desulfated, or de-esterified product to cancer cells; and generating an image of a part of said subject where cancer cells labeled by the dephosphorylated, desulfated, or de-esterified product reside, whereby enhanced contrast between normal tissue and cancerous tissue is provided by the dephosphorylated, desulfated, or de-esterified product.

The accompanying examples demonstrate that an underexplored generic difference between cancer and normal cells—verexpression of ectoenzymes having hydrolase activity, such as an ectophosphatase—triggers the D-tyrosine phosphate decorated magnetic nanoparticles ($Fe_3O_4$-p (D-Tyr)) to adhere selectively on cancer cells upon catalytic dephosphorylation. This enables magnetic separation of cancer cells from a mixed population of cells (e.g., co-cultured cancer cell and stromal cells), as well as other uses that involve selective labeling of cancer cells. Moreover, the $Fe_3O_4$-p(D-Tyr) nanoparticles also selectively inhibit cancer cells in the co-culture. As a general method to broadly target cancer cells without highly specific ligand-receptor interactions (e.g., antibodies), the use of the enzymatic reaction to spatiotemporally modulate the state of various nanostructures in cellular environment affords the theranostic applications of these nanomaterials. In addition to inhibiting survival of cancer cells decorated by the nanoparticles, these nanoparticles will also facilitate the hyperthermic killing of selectively labeled cancer cells in vivo by promoting localized heating of the tumor site. Finally, the enzymatically responsive nanoparticles afford a new type of contrast agent that can be used in imaging of tumors.

BRIEF DESCRIPTION OF THE DRAWINGS

FIG. 4A shows overlaid bright field and fluorescent microscope images of the HeLa-GFP cells (top) and HS-5 cells (bottom) magnetically captured by incubating the cells with MNP_pY (left) and MNP (right). The scale bar is 100 μm. FIG. 4B is a bar graph showing relative amount of cells (%) in the extraction or supernatant of all the cells collected after the treatment by 40 μg/mL MNP_pY and the magnetic capture. FIG. 4C shows M-H curves of MNP_pY or MNP on the cells after incubation with HeLa-GFP, HS-5 or the co-culture of HeLa-GFP and HS-5 cells. FIG. 4D shows relative amount of nanoparticles remained on the cells.

FIGS. 7A-B show quantification of phosphate on MNP_pY by using the phosphate assay. FIG. 7A shows a phosphate standard curve performed according to the phosphate assay. FIG. 7B shows amount of phosphate contained in 40 μg MNP_pY. The bar labeled MNP_pY+ALP indicates the amount of phosphate in MNP_pY solution treated with alkaline phosphatase ("ALP") after 24 hours. The bar labeled MNP_pY indicates the amount of phosphate liberated by MNP_pY in deionized $HO_2O$ after 24 hours.

FIGS. 8A-B show overlaid confocal fluorescent microscope images (×20 dry objective lens) of co-cultured HeLa-GFP and HS-5 cells treated with MNP_pY or MNP, respectively. For both figures, the left column of images indicates the extraction by magnetic field exposure and the right column of images indicates the supernatant recovered following such extraction. Cells were incubated with the growth medium, Dulbecco's Modified Eagle Medium, containing 40 μg/mL nanoparticles for 4 hours. After separation by magnet, the extraction fraction or supernatant fraction of cells were seeded back onto the confocal dishes. The initial number of cells is $1.0 \times 10^6$ per 6 cm culture dish. The scale bar is 100 μm.

FIGS. 9A-B show overlaid confocal fluorescent microscope images, at low magnification and high magnification, of HeLa-GFP cells treated with MNP_pY or MNP, respectively. For both treatments, MNP_pY (FIG. 9A) and MNP (FIG. 9B), the HeLa-GFP cells are shown at low magnification (left side, scale bar is 100 μm) or high magnification (right side, scale bar is 10 μm). The images here indicate the extraction of cells by magnet. Cells were incubated with the growth medium, Dulbecco's Modified Eagle Medium, containing 40 μg/mL nanoparticles for 4 hours. After separation by magnet, extracted cells were seeded back onto the confocal dishes. The initial number of cells is $1.0 \times 10^6$ per 6 cm culture dish.

FIG. 10 shows bright field microscope images (×20 dry objective lens) of HS-5 cells after incubation with MNP_pY (left) or MNP (right) and subsequent magnetic field extraction. Top images show cell distribution after extraction by the magnet. Bottom images show cell distribution in the supernatant. Cells were incubated with the growth medium, Dulbecco's Modified Eagle Medium, containing 40 μg/mL nanoparticles for 4 hours. After separation by magnet, the extraction fraction or supernatant fraction of cells were seeded back onto the confocal dishes. The initial number of cells is $1.0 \times 10^6$ per 6 cm culture dish. The scale bar is 100 μm.

FIGS. 12A-C are bar graphs showing relative cell viability as determined by cell counts. The co-culture of HeLa-GFP and HS-5 cells (FIG. 12A), HeLa-GFP cells (FIG. 12B), and HS-5 cells (FIG. 12C) were incubated with MNP_pY at the concentrations of 4, 10, 20, 40, 100 μg/mL (FIG. 12C). The results are scaled to the control, i.e., 100% represents the control containing 0 μg/mL of MNP_pY. The initial number of cells is $1.0 \times 10^4$/well.

FIGS. 14A-C are bar graphs showing relative cell viability as determined by cell counts. The co-culture of HeLa-GFP and HS-5 cells (FIG. 14A), HeLa-GFP cells (FIG. 14B), and HS-5 cells (FIG. 14C) were incubated with the MNP at the concentrations of 4, 10, 20, 40, 100 μg/mL. The results are scaled to the control, i.e., 100% represents the control containing 0 µg/mL MNP. The initial number of cells is $1.0 \times 10^4$/well.

FIGS. 15A-C show the results from the pretreatment of MNP_pY with ALP for 24 h to afford MNP_Y. FIG. 15A shows relative cell viability as determined by cell counts of the HeLa-GFP cells incubated with MNP_Y at the concentrations of 4, 10, 20, 40, 100 µg/mL. The results are scaled to the control, i.e., 100% represents the control containing 0 µg/mL MNP_Y. The initial number of cells is $1.0 \times 10^4$/well. FIG. 15B shows confocal fluorescent images (×20 dry objective lens) of HeLa-GFP cells treated with MNP_Y and subsequent magnetic field extraction. Left image shows cell distribution after extraction by the magnet; and the right image shows cell distribution in the supernatant. Cells were incubated with the growth medium, Dulbecco's Modified Eagle Medium, containing 40 µg/mL nanoparticles for 4 hours. After separation by magnet, the extraction fraction or supernatant fraction of cells were seeded back onto the confocal dishes. The initial number of cells is about $1.0 \times 10^6$ per 6 cm culture dish. The scale bar is 50 µm. FIG. 15C shows the amounts of cells (%) in the extraction fraction or supernatant fraction relative to the total number of cells collected after the treatment with 40 µg/mL MNP_Y and subsequent magnetic capture.

DETAILED DESCRIPTION OF THE INVENTION

Figure 1:
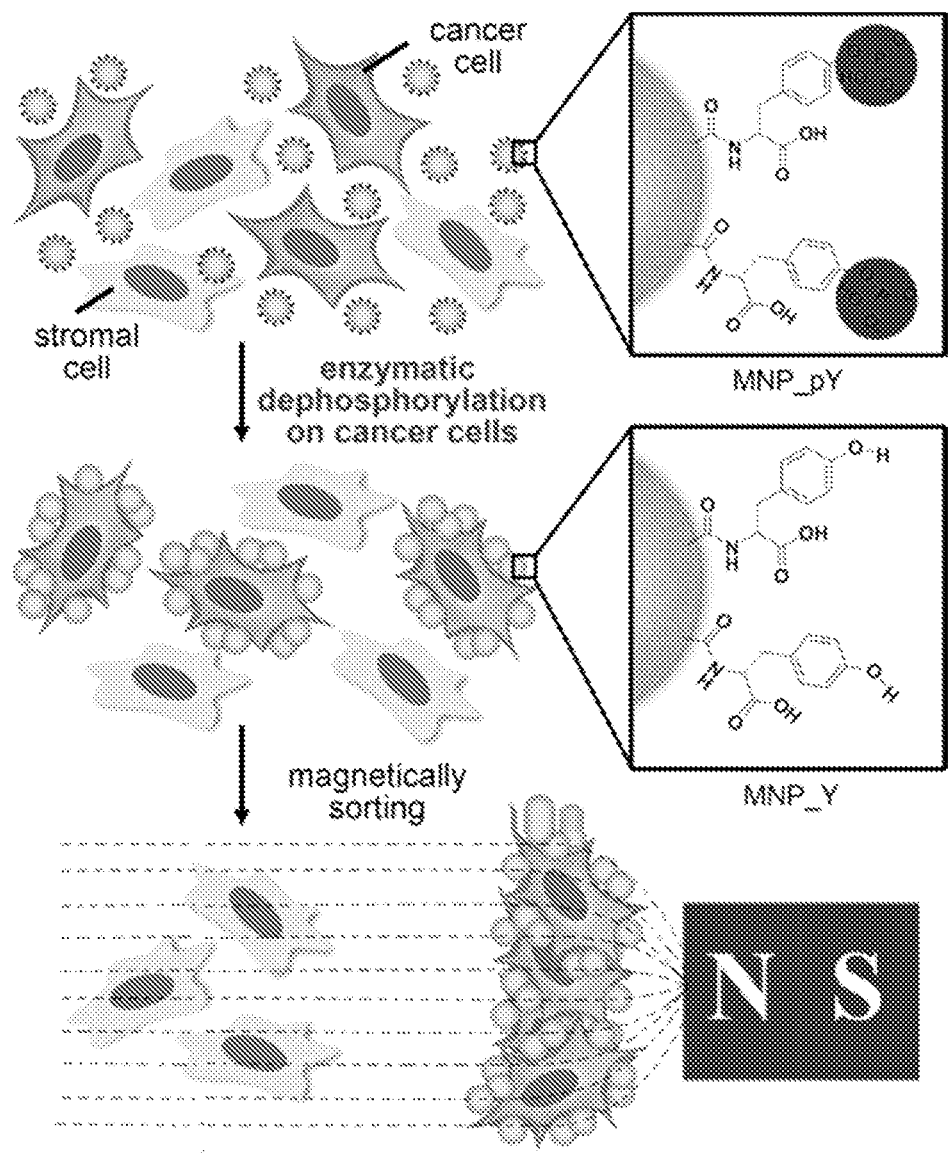
FIG. 1 illustrates schematically the enzymatic transformation of magnetic nanoparticles for selectively sorting cancer cells.

One aspect of the present invention relates to an enzymatically responsive product that includes an amino acid residue conjugated to a magnetic particle, wherein the amino acid residue is phosphorylated or sulfated or comprises an ester-moiety linked via peptide bond. Upon enzymatic cleavage of the phosphate, sulfate, or ester group from the amino acid by, e.g., an ectoenzyme expressed by or secreted by certain cells, the so-modified product is rendered capable of adsorption to the cell that expresses/secretes the ectoenzyme.

As used herein, "magnetic particle" refers to a microparticle or nanoparticle that exhibits magnetic behavior under one or more conditions. The magnetic particle can be ferromagnetic, paramagnetic, or superparamagnetic. Paramagnetic and superparamagnetic particles can be magnetized when exposed to an external magnetic field, but in the absence of the external magnetic field these particles do not retain their magnetic properties. Paramagnetic materials have a small, positive susceptibility to magnetic fields. The magnetic susceptibility of superparamagnetic particles is much larger than that of paramagnetic particles.

Any of a variety of magnetic particles can be employed in the present invention. In certain embodiments, the magnetic particles can be single material such as iron oxide (e.g., maghemite, $\gamma Fe_2O_3$, or magnetite, $Fe_3O_4$) or a mixture of a polymer and iron oxide. In alternative embodiments, the magnetic particle is in the form of a core/shell particle. Exemplary core materials include, without limitation, cobalt, iron or iron oxide, a cobalt/iron alloy, a nonmagnetic polymer, or a mixture of such metals or alloys with a polymer. Exemplary shell materials include, without limitation, graphene, an oxide, gold, silver, platinum, a polymer, or a mixture of a polymer and iron oxide.

A number of magnetic particles are commercially available including, without limitation, iron core/graphene shell particles available under the tradename TurboBeads® (Turbobeads LLC, Zurich, Switzerland), iron oxide/polymer particles available under the tradename Dynabeads® (Life Technologies, Eugene, Oreg.), iron oxide/polymer latex particles available under the tradename Estapor® (Merck Millipore, Billerica, Mass.), and magnetite/polystyrene shell on polystyrene core particles available under the tradename SPHERO™ Magnetic Particles (Spherotech, Lake Forest, Ill.).

In one embodiment, the product includes a single amino acid that is conjugated directly to the magnetic particle, and the amino acid is phosphorylated, sulfated, or linked by peptide bond to an ester moiety.

In another embodiment, the product includes a polypeptide containing from 2 to about 35 amino acids, and at least one of the amino acids is phosphorylated, sulfated, or linked by peptide bond to an ester moiety. In certain embodiments, two or more of the amino acids are phosphorylated or sulfated, or one or more amino acids is phosphorylated or sulfated and another amino acid is linked by peptide bond to an ester moiety. The phosphorylated, sulfated, or ester-linked amino acid residue can be conjugated directly to the magnetic particle or it can be linked via other amino acid residues in the polypeptide, one of which is conjugated directly to the magnetic nanoparticle.

The polypeptide can contain up to about 35 amino acids, up to about 30 amino acids, up to about 25 amino acids, up to about 20 amino acids, up to about 15 amino acids, up to about 10 amino acids, or between 2 to 10 amino acids.

In certain embodiments, the polypeptide can include anti-angiogenesis peptides.

In certain embodiments, the polypeptide can contain an amino acid sequence that includes a metalloprotease (MMP) cleavage site. Exemplary polypeptide sequences with an MMP cleavage site are shown in the table below.

| MMP | Precursor | SEQ. ID. NO: |
|---|---|---|
| MMP-1 | X-Gly-Pro-Gln-Gly↓Leu-Ala-Gly-Gln | 1 |
| MMP-2 | X-Ala-Pro-Ala-Ala↓Leu-Val-Gly-Ala | 2 |
| MMP-3 | X-Ala-Pro-Ala-Gly↓Leu-Lys-Ala-Pro | 3 |
| MMP-7 | X-Glu-Pro-Ala-Ser↓Leu-Arg-Ala-Gly | 4 |
| MMP-8 | X-Gly-Pro-Gln-Gly↓Leu-Arg-Gly-Arg | 5 |
| MMP-9 | X-Gly-Pro-Ala-Gly↓Leu-Arg-Gly-Pro | 6 |
| MMP-12 | X-Gly-Pro-Ala-Gly↓Leu-Gly-Ala-Ala | 7 |
| MMP-13 | X-Gly-Pro-Lys-Gly↓Leu-Arg-Gly-Gly | 8 |
| MMP-14 | X-Leu-Pro-Leu-Gly↓Leu-Val-Thr-Glu | 9 |

X: any aromatic group, aromatic amino acid residue, or hydrophobic amino acid;
↓: cleavage site.
Amino acid residues are proline (Pro), glutamine (Gln), glycine (Gly), leucine (Leu), alanine (Ala), valine (Val), lysine (Lys), glutamic acid (Glu), serine (Ser), arginine (Arg), threonine (Thr), and phenylalanine (Phe).

In certain embodiments, the polypeptide includes one or more aromatic amino acids. In alternative embodiments, the polypeptide contains only one aromatic amino acid. Exemplary aromatic amino acids include, without limitation, phenylalanine, phenylalanine derivatives, tyrosine, tyrosine derivatives, tryptophan, tryptophan derivatives, 1-naphthylalanine, and 2-naphthylalanine. In certain embodiments, not more than one aromatic amino acid is included or not more than two aromatic amino acids are included. In these embodiments, the polypeptide is generally not capable of acting as a hydrogelator, and self-assembling into nanostructures. Any known or hereinafter developed phenylalanine derivatives, naphthylalanine derivatives, tyrosine derivatives, or tryptophan derivatives can be used in the present invention. Exemplary derivatives of these amino acids include the addition of one or more ring substituents.

Other peptide variants include those described at Formula I in PCT Publication Nos. WO 2012/166705 and WO 2012/166706, both to Xu et al., which are hereby incorporated by reference in their entirety, where the nucleobase at the N-terminus of Formula I is instead replaced by the magnetic particle. Further peptide variants include those described at Formulae I and II in PCT Publication No. WO 2014/074789 to Xu et al., which is hereby incorporated by reference in its entirety, where the magnetic particle replaces the N-terminal group described therein or is instead conjugated to a Lys sidechain.

In certain embodiments, a phosphorylated amino acid residue is present alone (i.e., as a single amino acid conjugated to the magnetic particle) or present in the polypeptide. In larger polypeptides, more than one amino acid can be phosphorylated. The phosphorylated amino acid residue prevents selective adsorption of the magnetic particle to a cancer cell in the absence of dephosphorylation. Exemplary amino acids residues that are readily phosphorylated and catalytically dephosphorylated by an enzyme possessing hydrolase activity include, without limitation, serine, threonine, tyrosine, and histidine.

In certain embodiments, a sulfated amino acid is present alone (i.e., as a single amino acid conjugated to the magnetic particle) or in the polypeptide. The sulfated amino acid residue prevents selective adsorption of the magnetic particle to a cancer cell in the absence of desulfation. Exemplary amino acids residues that are readily sulfated and catalytically desulfated by an enzyme possessing hydrolytic activity include, without limitation, serine, threonine, tyrosine, and hydroxyproline.

In certain embodiments, a single amino acid is present alone (i.e., as a single amino acid conjugated to the magnetic particle) with an ester-moiety linked via peptide bond, or an amino acid in the polypeptide possesses an ester-moiety linked via peptide bond. The amino acid residue containing the ester-linked moiety prevents selective adsorption of the magnetic particle to a cancer cell in the absence of de-esterification. The amino acid residue to which an ester-moiety is linked via peptide bond can be any amino acid, whether or not the amino acid contains an aromatic side chain. In these embodiments, the ester-moiety can be any ester-containing compound that also possesses a primary amino group that can react with the C-terminal carboxylic acid to form a peptide bond. For example, 4-(2-aminoethyl)-4-oxobutanoic acid; 5-aminovaleric acid; 4-[(8-aminooctyl)amino]-4-oxobutanoic acid; 4-[(5-amino-1-oxopentyl)amino]butanoic acid; and 4-[(5-aminopentyl)amino]-4-oxobutanoic acid are suitable ester-containing moieties.

In certain embodiments, the amino acid residue can be catalyzed by all the ectoenzymes (e.g., ectohydrolase, ectophosphatase, ectosulfatase, and ectocarboxylesterase).

Although numerous oligopeptides are known to form supermolcular hydrogels, those containing multiple aromatic groups facilitate aromatic-aromatic interactions that likely stabilize the intermolecular hydrogen bonding in water to afford the hydrogels (Du et al., *Chem. Asian J.* 9(6):1446-1472 (2014), which is hereby incorporated by reference in its entirety). Examples include, without limitation, the conjugation of aromatic moieties (e.g., phenyl, naphthyl, fluorenyl, pyrenyl, cinnamoyl) via simple amide bond to both aromatic amino acids (e.g., phenylalanine, naphthylalanine, tyrosine, tryptophan) and non-aromatic amino acids residues. Thus, in certain embodiments, the peptide includes one or more amino acids and conjugates, or two or more amino acids, which may promote hydrogelation of the peptides.

In certain embodiments of the present invention, the peptide includes two or more amino acids that are incapable of hydrogelation, and the peptide is incapable of hydrogelation.

The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%. Similarly, where only one amino acid is used, the amino acid can be a D-amino acid or an L-amino acid.

As a consequence of utilizing entirely D-amino acids or a high proportion of D-amino acids, it is possible to render the peptide protease resistant, e.g., resistant to proteinase K digestion.

In certain embodiments, the peptide can include one or more amino acids whose side-chain is easily conjugated to the magnetic particle.

In certain embodiments, the peptide can include one or more amino acids whose side-chain is easily conjugated to, e.g., a fluorophore, a chemotherapeutic agent, an antiangiogenic agent, an immunomodulating agent, or an antigen. Numerous examples of each of these categories are well known in the art.

Exemplary amino acids that can be derivatized include lysine or arginine, whose terminal amino group of its side chain is reactive in conjugation procedures of the type described in the accompanying examples. Other conjugation protocols can be utilized with other amino acids, including aspartic and glutamic acid whose carboxylic acid groups are reactive in known conjugation procedures. Similarly, cysteine and cysteine derivatives can be used to form disulfide bonds during conjugation procedures. Allyl glycine can also be used in this regard.

In general, amino groups present in lysine side chains, as well as the N-terminal amino group, can be reacted with reagents possessing amine-reactive functional groups using known reaction schemes. Exemplary amine-reactive functional groups include, without limitation, activated esters, isothiocyanates, and carboxylic acids. Reagents to be conjugated include those listed above.

In general, guanidine groups present in arginine can be reacted with reagents possessing guanidine-reactive groups using known reaction schemes. Exemplary guanidine-reactive functional groups include, without limitation, NHS esters using gas phase synthesis (McGee et al., *J. Am. Chem. Soc.,* 134 (28):11412-11414 (2012), which is hereby incorporated by reference in its entirety).

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

In general, carboxyl groups present in glutamic or aspartic acid side chains, or at the C-terminal amino acid residue, can be reacted with reagents possessing carboxyl-reactive functional groups using known reaction schemes. Exemplary carboxyl-reactive functional groups include, without limitation, amino groups, amines, bifunctional amino linkers. Reagents to be conjugated include those listed above.

In each of the types of modifications described above, it should be appreciated that the conjugate can be directly linked via the functional groups of the peptide and the reagent to be conjugated, or via a bifunctional linker that reacts with both the peptide functional groups and the functional groups on the reagent to be conjugated.

The peptides of the present invention can be synthesized using standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. This can be followed with standard HPLC purification to achieve a purified peptide product.

Regardless of the embodiment, conjugation of the magnetic particles to the amino acid or polypeptide is carried out using carboxylic acid functionalized magnetic nanoparticles, which are activated using N-hydroxysuccinimide to form a peptide bond between the carboxylic acid on the magnetic particle and the amino group on the single amino acid residue or the N-terminal amino group of the polypeptide. This is illustrated schematically below, where the amino acid is shown in phosphorylated form (as opposed to sulfated or ester-linked):

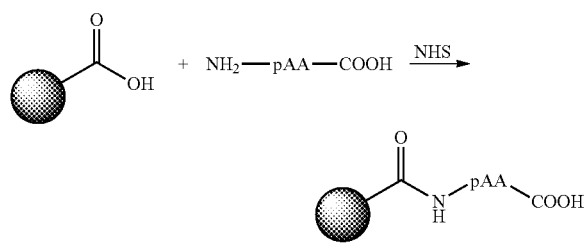

Similarly, a polypeptide containing a protected N-terminal group and bearing a reactive lysine sidechain can be coupled to the carboxylic acid functionalized magnetic nanoparticles, which are activated using N-hydroxysuccinimide to form a peptide bond between the carboxylic acid on the magnetic particle and reactive amino group of the lysine sidechain. This is illustrated schematically below, where a dipeptide containing phospho-tyrosine at the N-terminus of the polypeptide is shown:

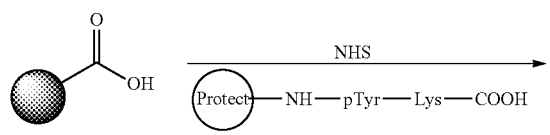

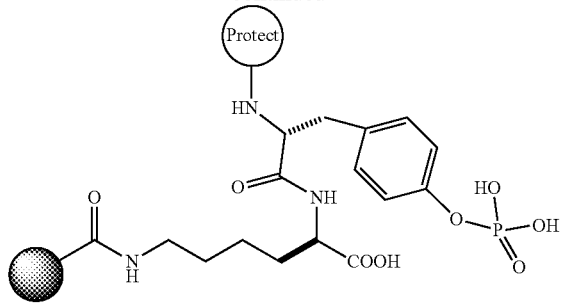

Deprotection of the illustrated dipeptide will afford a pTyr-Lys-MNP. This same reaction can be used, for example, with the dipeptide Lys-pTyr to afford MNP-Lys-pTyr with the MNP coupled to the sidechain rather than the N-terminus of the dipeptide. In addition, pTyr can be placed at any location of the peptides, which means that MNP-pTyr-Lys can be synthesized by using similar reactions. pTyr can also be replaced by pSer and pThr to generate MNP-Lys-pSer or MNP-Lys-pThr, respectively.

In certain embodiments, the magnetic particle includes an outer surface that is a polymer functionalized with one or more carboxylic acid groups, which are activated using N-hydroxysuccinimide to form a peptide bond between the carboxylic acid on the particle and the amino group on the single amino acid residue or the N-terminal amino group of the polypeptide. This is illustrated schematically below, where the amino acid is shown in phosphorylated form (as opposed to sulfated or ester-linked):

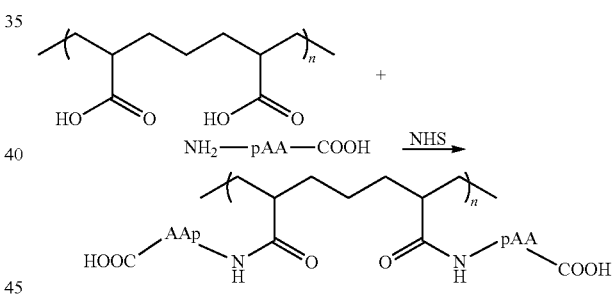

A further aspect of the present invention relates to pharmaceutical compositions that include a pharmaceutically acceptable carrier and an enzymatically responsive product of the present invention.

In certain embodiments, more than one peptide or amino acid can be provided per magnetic particle. For example, the magnetic particles can be labeled with from about 10 up to about 500 amino acids or peptides per particle, or about 50 up to about 400 amino acids or peptides per particle, or about 80 up to about 300 amino acids per particle. As demonstrated in the accompanying Examples, an average of about 124 phospho-D-Tyr were present on the magnetic particles used in those examples. In these embodiments, it is contemplated that multiple peptides or amino acids can be conjugated in a single step reaction. The different peptides can be similar in structure, but possess different conjugated agents as described above. In alternative embodiments, the peptides can be structurally distinct, including different primary amino acid sequences, and different conjugates.

In certain embodiments, the carrier is an aqueous medium that is well tolerated for administration to an individual, typically a sterile isotonic aqueous buffer. Exemplary aqueous media include, without limitation, normal saline (about 0.9% NaCl), phosphate buffered saline (PBS), sterile water/distilled autoclaved water (DAW), as well as cell growth medium (e.g., MEM, with or without serum), aqueous solutions of dimethyl sulfoxide (DMSO), polyethylene glycol (PEG), and/or dextran (less than 6% per by weight.)

To improve patient tolerance to administration, the pharmaceutical composition preferably has a pH of about 6 to about 8, preferably about 6.5 to about 7.4. Typically, sodium hydroxide and hydrochloric acid are added as necessary to adjust the pH.

The pharmaceutical composition suitably includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The composition may also include solubilizing agents, preservatives, stabilizers, emulsifiers, and the like. A local anesthetic (e.g., lidocaine) may also be included in the compositions, particularly for injectable forms, to ease pain at the site of the injection.

Effective amounts of the enzymatically responsive product will depend on the nature of use, including whether it is used for in vitro sorting of cancerous and noncancerous cells, or the nature of the cancerous condition which is being treated or imaged, as well as tumor volume, stage, and location(s). By way of example only, suitable concentrations may range from about 1 µM to about 500 mM, preferably about 10 µM to about 300 mM, about 50 µM to about 200 mM, or about 100 µM to about 100 mM. The volume of the composition administered, and thus, dosage of the peptide administered can be adjusted by one of skill in the art to achieve optimized results. This can be adjusted lower to identify the minimal effective dose, or tailored higher or lower according to the nature of the tumor to be treated or imaged.

According to one aspect the enzymatically responsive product can be used for separating distinct types of cells, i.e., those expressing or secreting an ectoenzyme from those that do not. This method includes exposing the enzymatically responsive product (or a composition containing the same) to a mixed population of cells including a first cell type that expresses an ectoenzyme that hydrolyzes the phosphate group, the sulfate group, or the ester-moiety of the enzymatically responsive product, and a second cell type that lacks an ectoenzyme that hydrolyzes the phosphate group, the sulfate group, or the ester-moiety of the enzymatically responsive product, whereby the product, after enzymatic cleavage of the phosphate, sulfate, or ester, selectively labels the first cell type after said exposing. Once selective labeling of the first cell type has occurred, it is then possible to separate the labeled first cell type from the second cell type. As noted above, in one embodiment the first cell type that expresses or secretes an ectoenzyme is a cancer cell and the second cell type is a non-cancerous cell.

Often, the mixed population of cells is obtained in the form of a biopsy of tissue suspected to contain cancerous tissue. The recovery and preparation of biopsy samples is well known in the art. Once the biopsy sample is obtained, the mixed cell population can be suspended in a suitable medium (e.g., buffer or growth medium) for subsequent exposure to the enzymatically responsive product or composition of the present invention.

The separation step involves introducing the exposed, mixed cell population to a magnetic field, wherein the labeled first cell type is retained within the magnetic field and the second cell type is not retained within the magnetic field, thereby separating the first and second cell types. This can be accomplished using a flow-through column, whereby the magnetic field retains the first cell type in the column and allows the second cell type to pass through the column for collection. Alternatively, a container containing aqueous medium can be exposed to the magnetic field and the first cell type collected in a region of the container, e.g., the bottom of the container, by manipulating the container within the magnetic field.

Thereafter, it is possible to remove from the container a supernatant containing the second cell type and then recover the second cell type from the supernatant. In certain embodiments, the supernatant is substantially free of or excludes the first cell type. If it is not, then this process can be repeated more than once.

Recovery of the second cell type may include, e.g., centrifuging the supernatant and obtaining a cell pellet that includes the second cell type. In certain embodiments, the cell pellet is substantially free of or excludes the first cell type. If it is not, then this process can be repeated more than once. Once the second cell type of the supernatant is recovered, it can be introduced into a growth medium and the second cell type grown for a period of time.

The retentate in the container is then collected and optionally re-processed to ensure that the second cell type is not present in the population of cells. In certain embodiments, the retentate is substantially free of or excludes the second cell type. Once the first cell type of the retentate is recovered, it can be introduced into a growth medium and the first cell type grown for a period of time.

Assessment of the cancerous state of the first cell type can be carried out using otherwise conventional procedures, including genotyping and cell surface marker analyses.

Various types of cancer cells express or secrete ectoenzymes of the types described above, which are suitable to activate the products of the present invention.

Other cell types that express or secrete ectoenzymes of the types described above are mammalian progenitor cells, virus-infected cells, bacterial pathogen, protozoa, and fungi. Some of the bacterial pathogens expressing an ectoenzyme are described in PCT Publication No. WO 02/10442 to Zyskind, which is hereby incorporated by reference in its entirety. Ectophosphatase activities have been reported in several microorganisms (Freitas-Mesquita et al., *Int. J. Mol. Sci.* 15:2289-2304 (2014), which is hereby incorporated by reference in its entirety), including protozoa such as *Leishmania* (Remaley et al., *Exp. Parasitol.* 60:331-341 (1985); De Almeida-Amaral et al., *Exp. Parasitol.* 114:334-340 (2006), which are hereby incorporated by reference in their entirety), *Trypanosoma* (Fernandes et al., *Z. Naturforschung* 52C:351-358 (1997); Meyer-Fernandes et al., *Z. Naturforschung* 54:977-984 (1999); Dos-Santos et al., *Int. J. Parasitol.* 42:819-827 (2012), which are hereby incorporated by reference in their entirety), and bacteria, such as *Mycobacterium bovis* (Braibant et al., *FEMS Microbiol. Lett.* 195:121-126 (2001), which is hereby incorporated by reference in its entirety). In fungi, ectophosphatases have been described in a large number of species (Freitas-Mesquita et al., *Int. J. Mol. Sci.* 15:2289-2304 (2014), which is hereby incorporated by reference in its entirety), including *Aspergillus fumigatus* (Bernard et al., *Microbiology* 148:2819-2829 (2002), which is hereby incorporated by reference in its entirety), and *Candida albicans* (Portela et al., *Oral Dis.* 16:431-437 (2010), which is hereby incorporated by reference in its entirety).

A further aspect of the invention relates to a method of treating cancer. This method includes administering to a subject having a cancerous condition a therapeutically effective amount of the enzymatically responsive product of the present invention or a composition containing the same, wherein the administration thereof is effective to cause selective adherence of the dephosphorylated, desulfated, or de-esterified product to cancer cells. As demonstrated in the accompanying examples, the selective adherence of the enzymatically modified product to cancer cells affects the growth or survival of cancer cells.

Exemplary subjects include any mammal that is susceptible to cancerous conditions including, without limitation, rodents, rabbits, canines, felines, ruminants, and primates such as monkeys, apes, and humans.

Administration of the enzymatically selective product or pharmaceutical composition can be carried out using any suitable approach. By way of example, administration can be carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. In certain embodiments, administration is carried out intralesionally, intratumorally, intradermally, or peritumorally. This administration can be repeated periodically, e.g., one or more times per month, one or more times per week, once daily, or twice daily. Optimal administration protocols can be established using routine skill.

In these several aspects of the invention, the cancer cells express a cell surface-bound phosphatase, secrete a phosphatase, or both; express a cell surface-bound sulfatase, secrete a sulfatase, or both; express a cell surface-bound esterase, secrete an esterase, or both; or any combination thereof. In these embodiments, the enzyme produced by the cancer cells is an ectoenzyme having hydrolytic activity, i.e., the enzyme hydrolyzes a phosphate group, a sulfate group, or a (carboxyl)ester group.

The cancer cells to be treated in accordance with these aspects can be present in a solid tumor, present as a metastatic cell, or present in a heterogenous population of cells that includes both cancerous and noncancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kapsosi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers).

Use of the disclosed products and compositions can be coordinated with previously known therapies. For instance, chemotherapeutic agents, immunotherapeutic agents, or radiotherapeutic agents, as well as surgical intervention can be used in a coordinated manner with the enzymatically selective product or pharmaceutical compositions of the present invention. Thus, a chemotherapeutic agent, an immunotherapeutic agent, or a radiotherapeutic agent can be administered to a patient before or after treatment with the peptides or pharmaceutical compositions of the present invention. Alternatively, surgical resection of a tumor can be carried out before or after treatment with the peptides or pharmaceutical compositions of the present invention.

Alternatively, hyperthermic treatment of tumors can be performed using the enzymatically selective product. After administration of the enzymatically selective product to an individual, a tumor-containing region of the subject's body can be exposed to an energy source suitable to cause thermal heating of the magnetic particles associated with the cancer cells and destruction of cancer cells. Exemplary energy sources include ultrasound, laser light, near infrared light, or alternating magnetic field (Chichel et al., *Rep. Pract. Oncol. Radiother.* 12(5):267 (2007); Day et al., *J. Biomech. Eng.* 131(7):074001 (2009); Kaddi et al., *Nanomedicine* 8(8): 1323 (2013); Elsherbini et al., *Internat'l J. Nanomed.* 6:2155 (2011), which are hereby incorporated by reference in their entirety).

Magnetic hyperthermia provides increased specificity by selectively accumulating nanoparticles in target tissues. The present invention presents an entirely novel approach for accumulation of the magnetic particles on tumor cell surfaces.

Magnetic particles induce local hyperthermia due to hysteresis heating in the presence of an alternating magnetic field (Alexiou et al., *J. Nanosci. Nanotech.* 6:2762 (2006), which is hereby incorporated by reference in its entirety). The resulting induced flux reversal dissipates energy as heat only in the region of magnetic material localization allowing a highly localized increase in temperatures thus avoiding the normal tissues. The extent of temperature rise depends upon magnetic properties of the particles, magnetic field strength, frequency of oscillation, and cooling capacity of the blood flow in the tumor site (Gupta and Gupta, *Biomaterials* 26:3995 (2005), which is hereby incorporated by reference in its entirety). Cellular inactivation is achieved when temperatures exceed 42° C. for >30 minutes; temperatures>46° C. cause extensive cellular necrosis (thermoablation) (Pankhurst et al., *J. Physics D: Applied Physics* 36:R167 (2003), which is hereby incorporated by reference in its entirety).

Yet another aspect of the invention relates to a method for imaging cancer cells. This method includes administering to a subject having a cancerous condition an enzymatically selective product of the invention or a composition containing the same, wherein said administering is effective to cause the product to contact cancer cells that express a cell surface-bound phosphatase or sulfatase, secrete a phosphatase or sulfatase, or both, and cause selective adherence of the dephosphorylated, desulfated, or de-esterified product to cancer cells. Thereafter, it is possible to use the magnetic particles, now selectively adsorbed to the cancer cells, as a contrast agent during magnetic resonance imaging. Generating a magnetic resonance image of a part of the subject where labeled cancer cells reside allows for enhanced contrast between normal tissue and cancerous tissue.

Superparamagnetic contrast agents have greater magnetic susceptibility than traditional MRI contrast agents (e.g., gadolinium) and some are commercially available, such as suspensions of polymer-coated ferromagnetic nanoparticles in water (Alexiou et al., *J. Nanosci. Nanotechnol.* 6:2762-2768 (2006), which is hereby incorporated by reference in its entirety). Their presence significantly weakens the MRI signal and creates a negative enhancement effect on images. MRI-enhancing contrast agents include superparamagnetic iron oxide (SPIO, >50 nm) and ultrasmall superparamagnetic iron oxide (USPIO, <50 nm) particles (Couvreur and Vauthier, *Pharmaceutical Research* 23:1417 (2006), which is hereby incorporated by reference in its entirety). Sequestration of SPIO nanoparticles by the reticulo-endothelial system provides high contrast imaging of splenic/hepatic tumors and metastases. USPIO nanoparticles have longer circulation times in the blood and broader tissue distribution because they avoid reticulo-endothelial system sequestration; they are ideal for detecting metastases in lymph nodes. The present invention presents an entirely novel approach for accumulation of the magnetic particles on tumor cell surfaces.

U.S. Pat. No. 5,869,023 to Ericcson, which is hereby incorporated by reference in its entirety, describes a method for magnetic resonance imaging using positive and negative contrasting agents. The same approach can be used with the products of the present invention as contrast agents.

EXAMPLES

The following examples are intended to illustrate the present invention, but are not intended to limit the scope of the appended claims.

Example 1—Instruments

Transmission electron microscope (TEM) images were taken on Morgagni 268 transmission electron microscope. Confocal images were obtained on a Leica TCS SP2 Spectral Confocal Microscope. Magnetic studies were carried out using a Lakeshore 7404 high sensitivity vibrating sample magnetometer (VSM). Samples were dried with Labconco Freezone 4.5 Plus vacuum lyophilizer. The cells were counted by Bio-Rad TC 20™ Automated cell counter.

Example 2—Phosphate Assay

The phosphate assay kit (colorimetric) (ab65622, abcam) was utilized to quantify the amount of phosphate on MNP_pY. First, the phosphate standard curve was obtained. 10 µl of the 10 mM phosphate standard was diluted with 990 µl dH$_2$O and mixed well to generate 100 µM working phosphate standard. After adding 0, 10, 20, 30, 40, 50 µl of the 100 µM working phosphate standard to one 96 well plate, the volume was adjusted to 200 µl with dH$_2$O to generate 0, 1, 2, 3, 4, 5 nmol of phosphate standard. Prior to reading the absorbance at 620 nm using a plate reader, 30 µl phosphate reagent was added into all standard wells and the mixture was incubated at room temperature for 30 minutes. When the amount of phosphate on MNP_pY was quantified by following similar protocol. First, 40 µg MNP_pY was incubated with 100 µl dH$_2$O or 100 µl dH$_2$O containing 30 U alkaline phosphatase ("ALP") for 24 hours. After centrifugation, 20 µl of the treated solution was taken out and the volume was adjusted to 200 µl with dH$_2$O. After the treatment with 30 µl phosphate reagent for 30 minutes at room temperature, the absorbance was read by using a plate reader.

The result indicated that the absorbance of 20 µl solution treated with ALP is 1.36 and that of 20 µl solution just with dH$_2$O is 0.2843. According to the phosphate standard curve shown in FIG. 7, it was concluded that there are 6.829 nmol tyrosine phosphates in 20 µl treated solution. Since MNP_pY was incubated with 100 µl dH$_2$O containing ALP, there are at least 34.145 nmol tyrosine phosphates on 40 µg MNP_pY. According to the data from iron oxide nanoparticles (NanoTech Ocean), there are 6.9 nmol particles of 1 mg iron oxide, which means 40 µg MNP_pY contains 0.276 nmol nanoparticles. Followed by this estimation, it was concluded that there are at least 34.145 nmol tyrosine phosphates on 0.276 nmol MNP_pY nanoparticles, which indicated that there are at least 124 D-tyrosine phosphate molecules on each MNP_pY nanoparticle.

Example 3—Cell Culture

All cell lines were purchased from the American Type Culture Collection (ATCC, Manassas, Va., USA). The HeLa-GFP and HS-5 cells were propagated in Dulbecco's Modified Eagle Medium (DMEM, high glucose, Invitrogen Life Technologies 10829-018) supplemented with 10% fetal bovine serum (FBS, Invitrogen Life Technologies 10082-147), 100 U ml$^{-1}$ penicillin and 100 µg ml$^{-1}$ streptomycin (Invitrogen Life Technologies 15070-063) in a fully humidified incubator containing 5% $CO_2$ at 37° C.

Example 4—Confocal Microscopy $1.0 \times 10^6$ cells in exponential growth phase were seeded in 6 cm cell culture dish. The cells were allowed for attachment for 12 hours at 37° C., 5% $CO_2$. The culture medium was removed, and new culture medium containing MNP_pY or MNP at 40 µg/mL was added. After 4 hours of incubation, cells were washed with growth medium 3 times and detached with 0.25% (w/v) Trypsin-0.53 mM EDTA solution. After harvesting the cells (FIG. 2), one magnet was used to collect extraction from supernatant and rinsed each group of cells three times with growth medium before seeding them back onto the confocal dishes. With four-hour attachment, the cells were rinsed three times in PBS, and then kept in the PBS buffer for imaging.

Example 5—Magnetic Characterization

Similar to the method for confocal microscopy, $1.0 \times 10^6$ cells were treated with growth medium containing 200 µg MNP_pY or MNP for 4 hours, and then washed with growth medium 3 times and detached with 0.25% (w/v) trypsin-0.53 mM EDTA solution. The collected cell pellets after centrifugation were dried with the vacuum lyophilizer. Magnetic studies were carried out using a Lakeshore 7404 high sensitivity vibrating sample magnetometer (VSM) with fields up to 1.5 tesla at room temperature.

Example 6—Cell Viability Assay

Cells in exponential growth phase were seeded in a 96 well plate at a concentration of $1.0 \times 10^4$ cell/well. The cells were allowed to attach to the wells for 12 hours at 37° C., 5% $CO_2$. The culture medium was removed and 100 µL of the culture medium containing compounds (immediately diluted from fresh prepared stock solution of 10 mM) at gradient concentrations (0 µM as the control) was placed into each well. After culturing at 37° C., 5% $CO_2$ for 24, 48, 72 hours, the growth medium from each well was removed and 50 µL 0.25% (w/v) trypsin-0.53 mM EDTA solution was added. 4 minutes later, the cells were counted by using automated cell counter. Data represents the mean±standard deviation of three independent experiments.

Discussion of Examples 1-6

Encouraged by the seminal work on the DNA linked gold nanoparticles to report DNA hybridization (Mirkin et al., Nature 382:607 (1996); Cao et al., Science, 297:1536 (2002); Rosi et al., Chem. Rev. 105:1547 (2005); Taton et al., Science 289:1757 (2000), which are hereby incorporated by reference in their entirety) and the recent work on the dispersion of peptide coated gold nanoparticles to detect a specific enzyme (Jia et al., Anal. Chem. 74:2217 (2002); Liu et al., J. Am. Chem. Soc. 125:6642 (2003); Laromaine et al., J. Am. Chem. Soc. 129:4156 (2007), which are hereby incorporated by reference in their entirety), and based on unexpected observation of selective formation of pericellular nanonets on cancer cells upon dephosphorylation of D-peptides catalyzed by ectophosphatases (Kuang et al., Angew. Chem., Int. Ed. 53(31):8104 (2014), which is hereby incorporated by reference in its entirety), enzymatic transformation ("ET") was used to trigger the adhesion of iron oxide nanoparticles on cells for sorting cancer cells. Enzymatic reactions were selected over antibodies to distinguish cancer and normal cells for three reasons: (i) the overexpression of ectophosphatases on the surface of cancer cells represents a generic difference between many cancer and normal cells (Fishman et al., Nature 219:697 (1968); Pospisil et al., BMC Bioinformatics 7:11 (2006), which are hereby incorporated by reference in their entirety); (ii) the omission of antibodies reduces the cost and increases the stability of agents; (iii) being highly efficient and specific, enzymatic reactions offer a simple, fast yet fundamentally new way to modulate the surface chemistry of magnetic nanoparticles (Sun et al., Nano Lett. 3:955 (2003); Sun et al., Anal. Chem. 74:5297 (2002); Yang et al., J. Am. Chem. Soc. 136:8153 (2014), which are hereby incorporated by reference in their entirety) for spatiotemporally defining the magnetic nanoparticles in cellular environment, which is less explored.

Figure 2:
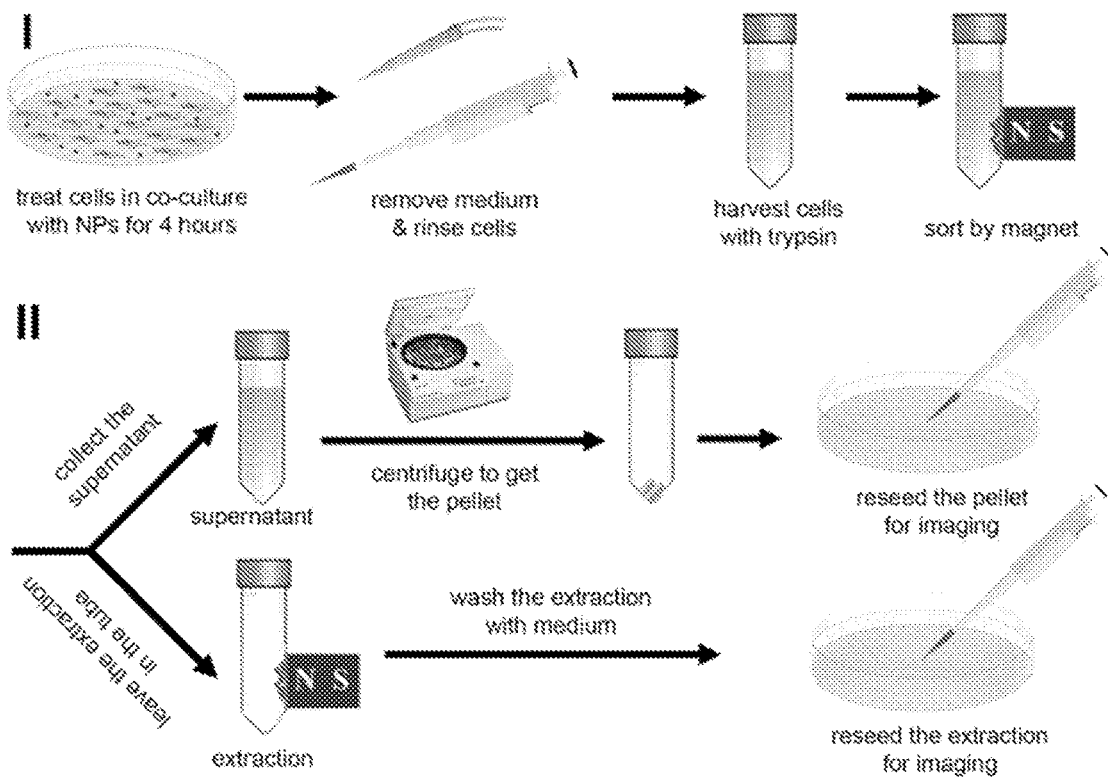
FIG. 2 illustrates schematically a procedure for the separation of cancer cells from co-culture of cancer and stromal cells.

Iron oxide nanoparticles (FIG. 1) were decorated with a simple amino acid, D-tyrosine phosphate, to engineer the biofunctional magnetic nanoparticle ($Fe_3O_4$-p(D-Tyr), MNP_pY). Ectophosphatases (e.g., placental alkaline phosphatase (ALPP) overexpressed on the surface of cancer cells (Pospisil et al., BMC Bioinformatics 7:11 (2006), which is hereby incorporated by reference in its entirety) catalyze the dephosphorylation of phosphate-bearing magnetic nanoparticles (MNP_pY) to form tyrosine coated magnetic nanoparticles ($Fe_3O_4$-(D-Tyr), MNP_Y). Microscopic studies confirmed that, upon the enzymatic transformation, MNP_Ys adhered selectively on the surface of cancer cells, which allowed a small magnet to capture the cancer cells from a mixture of cancer and stromal cells (FIG. 2). Moreover, cell viability study indicated that MNP_pY selectively inhibits the growth of cancer cells in the co-culture that mimics tumor microenvironment (Hanahan et al., Cell 144:646 (2011), which is hereby incorporated by reference in its entirety). As a new approach for selectively targeting and sorting cancer cells, this exceptionally simple method not only illustrates a straightforward, selective, and inexpensive procedure for sorting cancer cells, but will also lead to the application of nanoparticles, based on the spatiotemporal distribution of a specific enzyme, for disease diagnosis and treatment.

Figure 6:
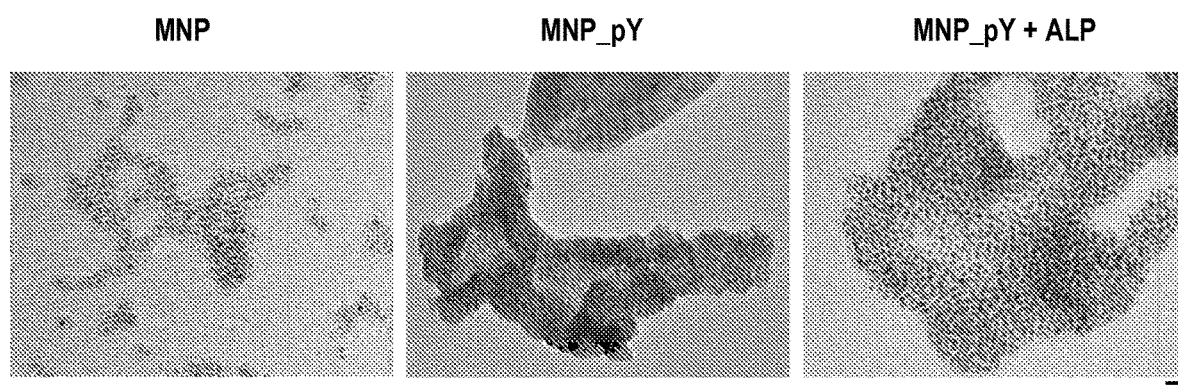
FIG. 6 shows transmission electron microscope (TEM) images of iron oxide nanoparticles MNP (Left), MNP_pY (Middle), and MNP_pY+ALP. The nanoparticles are dissolved in water at the concentration of 2,000 μg/mL (pH=7.4). The scale bar is 20 nm.

The synthesis of MNP_pY is fast and straightforward. Using the well-established iron oxide nanoparticles (Sun et al., J. Am. Chem. Soc. 126:273 (2004); Hyeon et al., J. Am. Chem. Soc. 123:12798 (2001), which are hereby incorporated by reference in their entirety) that are surface-functionalized with carboxylic acid groups (and are commercially available), the nanoparticles were directly coupled to D-tyrosine phosphate using N-hydroxysuccinimide (NHS) to activate the carboxylic acid groups. Following three times rinsing by methanol and water, respectively, centrifugation separated the final MNP_pY dispersed in water for use. Transmission electron microscopy confirmed that there was little morphological change of the iron oxide nanoparticles before and after functionalization by D-tyrosine phosphates (FIG. 6). The quantification of phosphate on MNP_pY by using the phosphate assay indicated that there are at least 124 D-tyrosine phosphate molecules on each MNP_pY nanoparticle (FIG. 7).

A process for the sorting of cancer cells from the cell mixture is shown in Stage I of FIG. 2. After seeding $1.0 \times 10^6$ HeLa-GFP (Platani et al., J. Cell Biol. 151:1561 (2000), which is hereby incorporated by reference in its entirety) and HS-5 (McMillin et al., Nat. Med. 16:483 (2010), which is hereby incorporated by reference in its entirety) cells per culture dish (6 cm) overnight, MNP_pY (40 µg/mL) was added to incubate the co-culture cells for 4 hours. After removing the growth medium containing nanoparticles and rinsing the cells three times, trypsin solution (0.25% (w/v) in 0.53 mM EDTA was used to help the detachment of the cells. Following aspirating the cells to obtain the cell suspension by gently pipetting, a small magnet was placed outside the Eppendorf tube for 1 min to divide the cell suspension into two portions: supernatant and extraction. After the centrifugation and rinsing of the supernatant or extraction fractions, the pellets of cells were reseeded onto confocal petri dishes (stage II, FIG. 2) for imaging which acted as a way to verify the results of the sorting.

Figure 3:
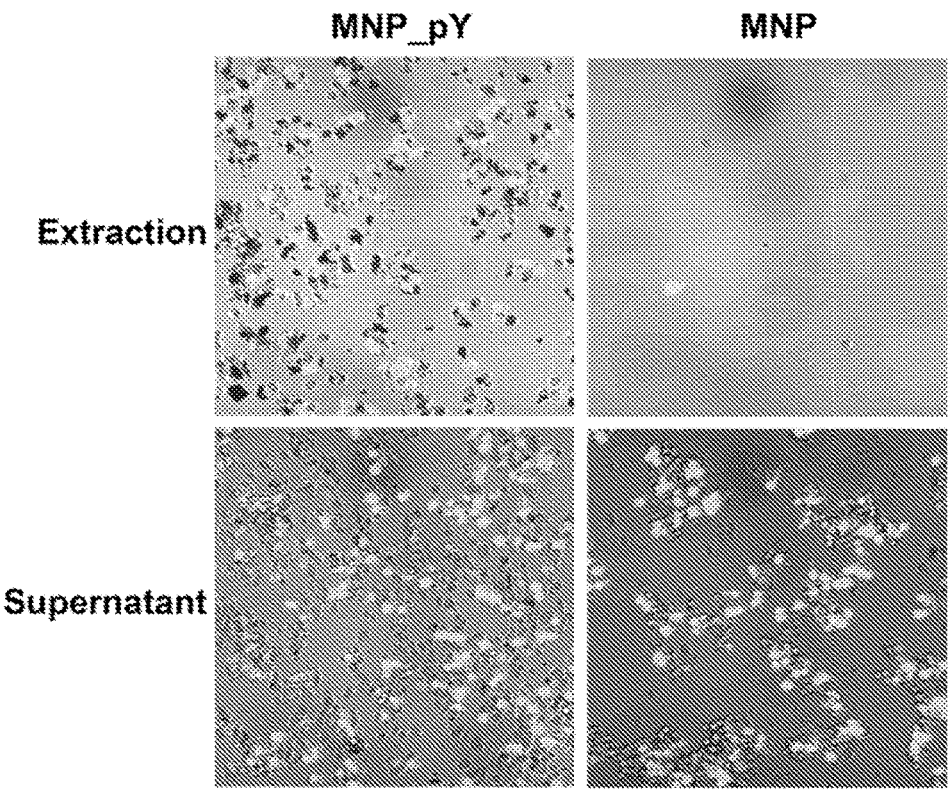
FIG. 3 shows overlaid bright field and fluorescent images (×20 dry objective lens) of the extraction and supernatant portions of cells after adding phosphotyrosine-labeled magnetic (iron oxide) nanoparticles ("MNP_pY", left) and unlabeled magnetic (iron oxide) nanoparticles ("MNP", right) to the co-culture of HeLa-GFP and HS-5 cells for magnetic sorting. Cells were incubated with the growth medium, Dulbecco's Modified Eagle Medium (DMEM), containing 40 μg/mL nanoparticles for 4 hours (top: the cells extracted by magnet; bottom: the cells remained in supernatant). The initial number of cells is $1.0 \times 10^6$ per 6 cm culture dish. The scale bar is 100 μm.

FIG. 3 shows the results of the sorting of HeLa-GFP cells from the co-culture of HeLa-GFP and HS-5 cells that mimics tumor microenvironment (McMillin et al., Nat. Med. 16:483 (2010), which is hereby incorporated by reference in its entirety). After the treatment by MNP_pY and the magnetic capture, most of the cells from the extraction portion exhibited bright green fluorescence, indicating that they are cancer cells (i.e., HeLa-GFP). On the contrary, the majority of the cells from the supernatant lacked of green fluorescence, indicating that they are HS-5 stromal cells. The bright field images (FIG. 8) show that many magnetic nanoparticles (MNP_Y) adhere on the surface of the cancer cells extracted by the magnet, which likely results from the dephosphorylation of D-tyrosine phosphate on the iron oxide nanoparticles by the overexpressed ectophosphatases on the surface of cancer cells. To confirm that enzymatic transformation ("ET") is responsible for the capture of the cancer cells, MNP were used as a control by repeating the procedure shown in FIG. 2. After the treatment by MNP and magnetic sorting, almost no cell was observed from the extraction portion after reseeding, but the corresponding supernatant (i.e., from the sample treated by MNP) contained (almost) all the fluorescent (HeLa-GFP) and non-fluorescent (HS-5) cells. Agreeing with this observation, after the incubation of the cells with the control iron oxide nanoparticles (MNP), the bright field images revealed that none of the MNP adheres on the surface of cancer or stromal cells (FIG. 8). These results, together, indicate that MNP_pYs, being catalytic dephosphorylated by the ectophosphatases overexpressed on the cancer cells, are suitable for magnetically and selectively sorting cancer cells from co-culture of cancer and stromal cells.

To further confirm the selectivity of MNP_pY towards cancer cells, HeLa-GFP and HS-5 cells were used separately as the control cells and the procedure shown in FIG. 2 was repeated. The overlaid bright field and fluorescent images in FIG. 4A indicate that, after the cells being incubated with MNP_pY and subjected to magnetic sorting, the extraction portion only contains HeLa-GFP cells (as proved by the bright green fluorescence from the cancer cells). The bright field images (FIG. 9) also confirmed that MNP-Ys adhere on the surface of HeLa-GFP cells. The incubation of MNP_pY with HS-5 cells hardly results in HS-5 cells in the extraction portion, and there is no nanoparticles on the HS-5 cells in the supernatant (FIG. 10). Similar to the observation in the incubation of MNP with the co-culture, the use of MNP on separately cultured HeLa-GFP or HS-5 captured neither GFP-HeLa nor HS-5 cells (FIG. 4A) in the extractions.

Figure 4:
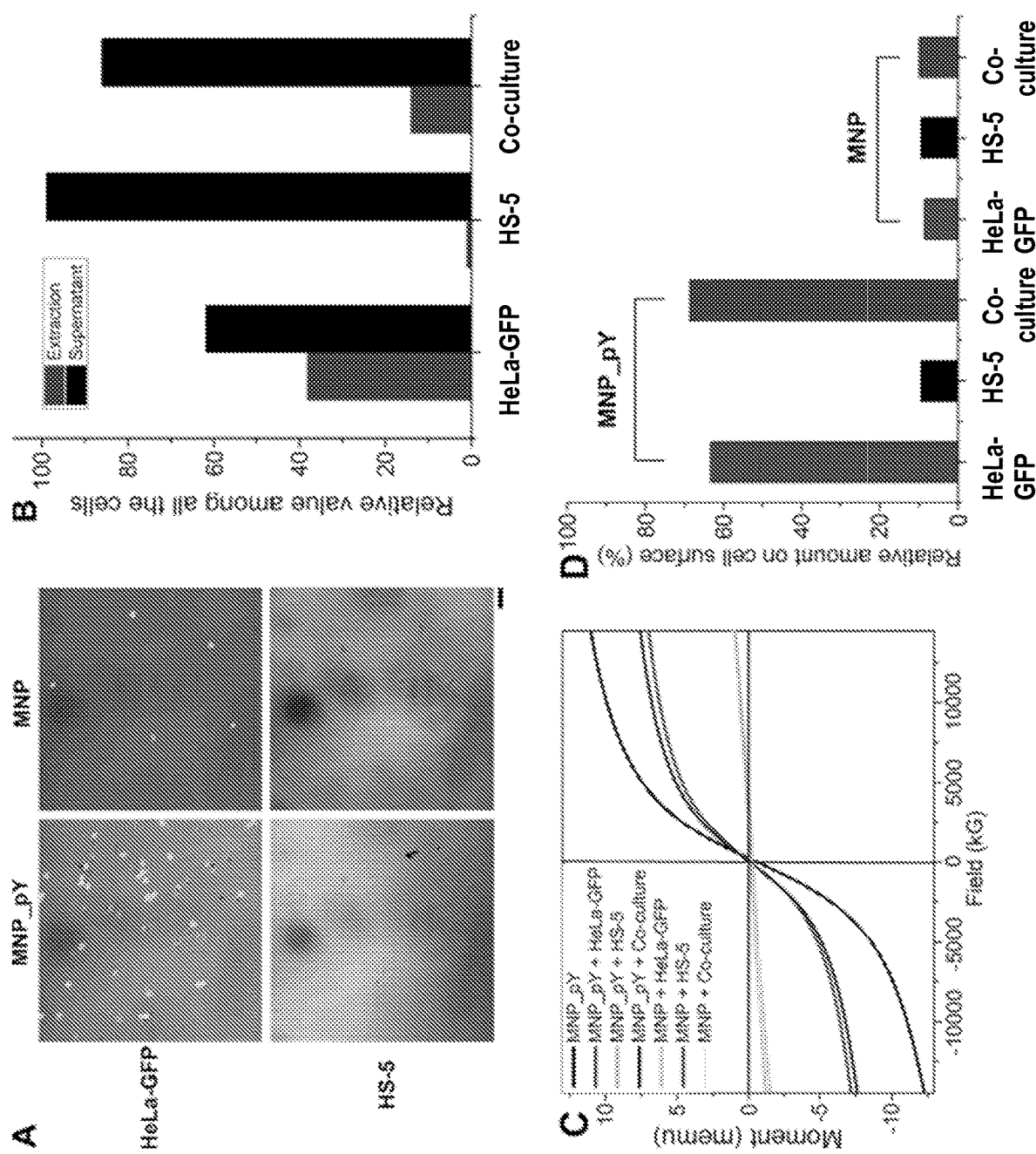
FIGS. 4A-D illustrate the selectivity of MNP_pY towards cancer cells.

To quantify the efficiency of cell capture of MNP_pY, the cell numbers were counted in the extraction or the supernatant fractions. As shown in FIG. 4B, the addition of 100 µg of MNP_pY in the co-culture of $6.6 \times 10^5$ total cells (with the initial ratio of HeLa-GFP and HS-5 cells in co-culture to be 1:10), 14% of cells is captured from the mixed cells, which indicated that this method separates over 90% of the cancer cells from the co-culture. This conclusion was reached, because (i) MNP_pY hardly capture any HS-5 cells (i.e., less than 1%, FIG. 4B); (ii) HeLa-GFP cells proliferate faster than HS-5 cells do; (iii) the addition of 100 µg of MNP_pY in the culture of initially $6.0 \times 10^5$ HeLa-GFP cells allowed the capture of $3.0 \times 10^5$ cells (about 3000 cells/µg MNP_pY, which is consistent with VSM measurement (vide infra)).

Figure 11:
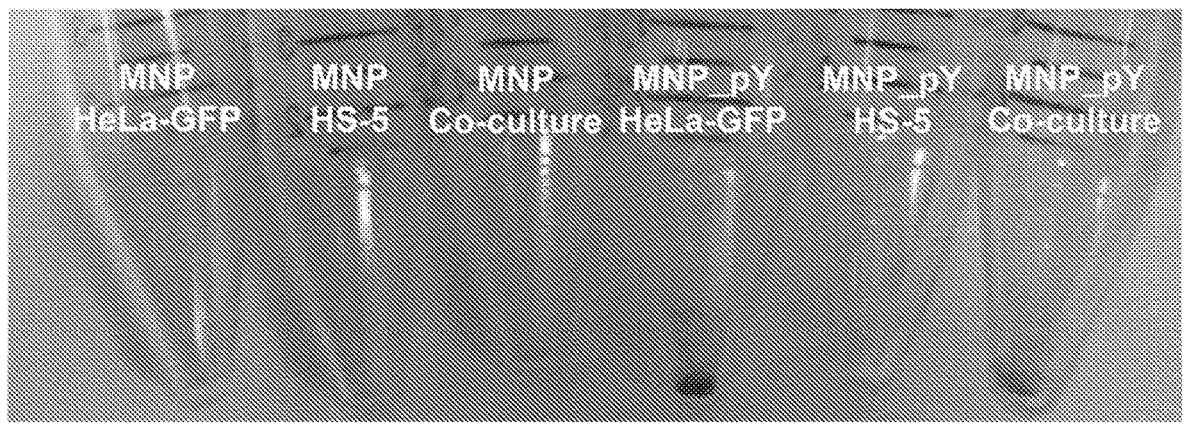
FIG. 11 shows optical images of pellets collected from co-culture of HeLa-GFP and HS-5 cells, HeLa-GFP cells, or HS-5 cells treated with 200 μg MNP_pY or MNP. The initial number of cells is $1.0 \times 10^6$ per 6 cm culture dish.

Magnetic properties of the iron oxide nanoparticles were studied by using a vibrating sample magnetometer ("VSM") for quantifying the amount of MNP_Y remained on the cells. As shown in FIG. 4C, 200 µg of MNP_pY has the magnetic moment of 11.0 memu, which can serve as a reference for estimating the magnetic nanoparticles on the cells. After incubated with co-culture of HeLa-GFP and HS-5 cells with same amount of MNP_pY for 4 hours, the magnetic moment of nanoparticles remained on all of the cells is decreased to 7.6 memu, which is around 69% of all the MNP_pY before the treatment (FIG. 4D). Moreover, when the MNP_pYs were incubated with only the HeLa-GFP cells, the moment of MNP_Y on the cell surface was 7.0 memu, suggesting that 63% of nanoparticles adhere to the HeLa-GFP cells. This quantity is comparable to the amount of MNP_Y on the HeLa-GFP in the co-culture. On the other hand, the incubation of MNP_pY with HS-5 cells only resulted in a magnetic moment of 1.0 memu, which is 9% of all the MNP_pY before the treatment, thus confirming that HS-5 cells hardly absorb MNP_pY. These results are compatible with the optical images of the pellets collected with the treatment of nanoparticles (FIG. 11). According to cell numbers and the magnetic moments, it was estimated that the capture efficiency is about 7000 cells/µg MNP_pY, which is comparable to the efficiency obtained by counting numbers of captured cell. The measurement of the cells treated only by MNPs (FIGS. 4C and 4D) confirmed that there were few control iron oxide nanoparticles (MNP) remaining on the surface of any cells.

Figure 5:
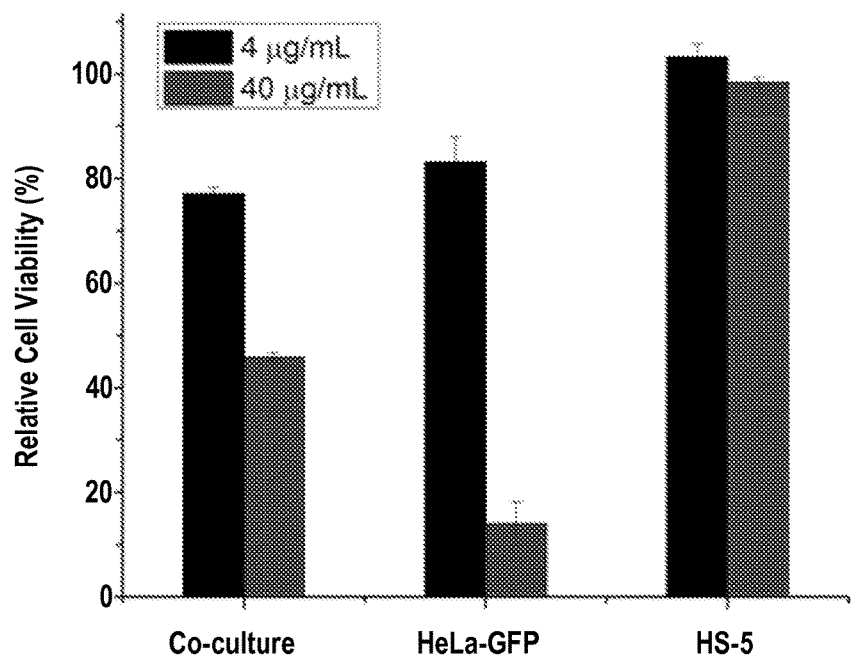
FIG. 5 is a graph showing relative cell viability (determined by counting the cell numbers; 100% represents the control, i.e., 0 μg/mL of the compound) of co-culture of HeLa-GFP and HS-5 cells, HeLa-GFP cells, and HS-5 cells incubated with MNP_pY at the concentrations of 4 and 40 μg/mL. The initial number of cells is $1.0 \times 10^4$/well.
Figure 13:
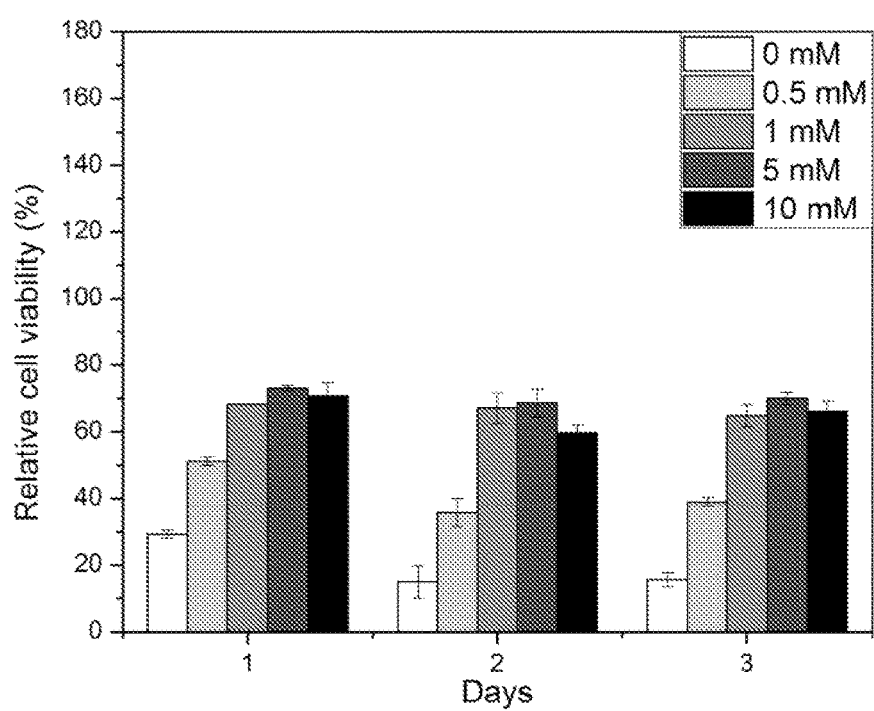
FIG. 13 shows relative cell viability as determined by cell counts. HeLa-GFP cells were incubated with 40 μg/mL MNP_pY and different concentration of L-phenylalanine (e.g., 0, 0.5, 1, 5, 10 mM). The results are scaled to the control, i.e., 100% represents the control containing 0 μg/mL of MNP_pY. The initial number of HeLa-GFP cells is $1.0 \times 10^4$/well.

Besides selectively capturing cancer cells in co-culture, MNP_pY selectively inhibited the proliferation of cancer cells. As shown in FIG. 5, being incubated with different concentrations of MNP_pY, the viability of co-culture of HeLa-GFP and HS-5 cells (measured by counting the cell number) is much less than that of control. When the concentration is larger than 20 µg/mL, the cell viability remains almost the same, which indicates that the stromal cells are still alive while most of cancer cells are killed by MNP_pY (FIG. 12). This result agrees with the viability of the homogeneous cells treated by MNP_pY. After being treated by different concentrations of MNP_pY, the proliferation of HeLa-GFP cells shows significant inhibition, especially when the concentration of MNP_pY is larger than 10 µg/mL. Cell viability studies indicated that MNP_pY inhibited the growth of HeLa-GFP cells with the $IC_{50}$ value of 12 µg/mL (10.2 µM tyrosine phosphate) at 48 hours. On the contrary, after being treated by the same concentrations of MNP_pY, HS-5 cells keep almost the same proliferation with the control, which indicated that MNP_pY has no cytotoxicity to the stromal cells (e.g., HS-5). When HeLa-GFP cells are treated with 40 µg/mL of MNP_pY and different concentrations of L-phenylalanine (e.g., 1, 5, 10 mM), a known inhibitor of ALPP (Fernley et al., *Biochem. J.,* 116:543 (1970), which is hereby incorporated by reference in its entirety), more than 60% of cells remain alive (FIG. 13). In addition, the incubation of MNP with HeLa-GFP or HS-5 cells hardly inhibited the cell proliferation (FIG. 14). These results indicated that ALPP is largely responsible for converting MNP_pY to MNP_Y on cancer cell surface, and for selectively sorting and inhibiting cancer cells.

To further demonstrate that enzymatic transformation of MNP_pY is the key point for selective sorting of cancer cells, MNP_Y was utilized in a separate experiment. MNP_Y resulted from the treatment of MNP_pY with ALP prior to incubating with cells, and the procedure shown in FIG. 2 was then repeated. According to cell viability test, MNP_Y itself shows little cytotoxicity to cells (FIG. 15A). And as shown in FIG. 15B, almost no cell was observed from the extraction fraction while all cells remained in the corresponding supernatant fraction (FIG. 15C). These results confirmed that, although the treatment of MNP_pY with phosphatases will generate MNP_Y, it is ET of MNP_pY by overexpressed ectophosphatases at the surface of cancer cells, not MNP_Y itself, that triggers the magnetic separation and selectively inhibition of cancer cells from co-culture circumstance.

Figure 16:
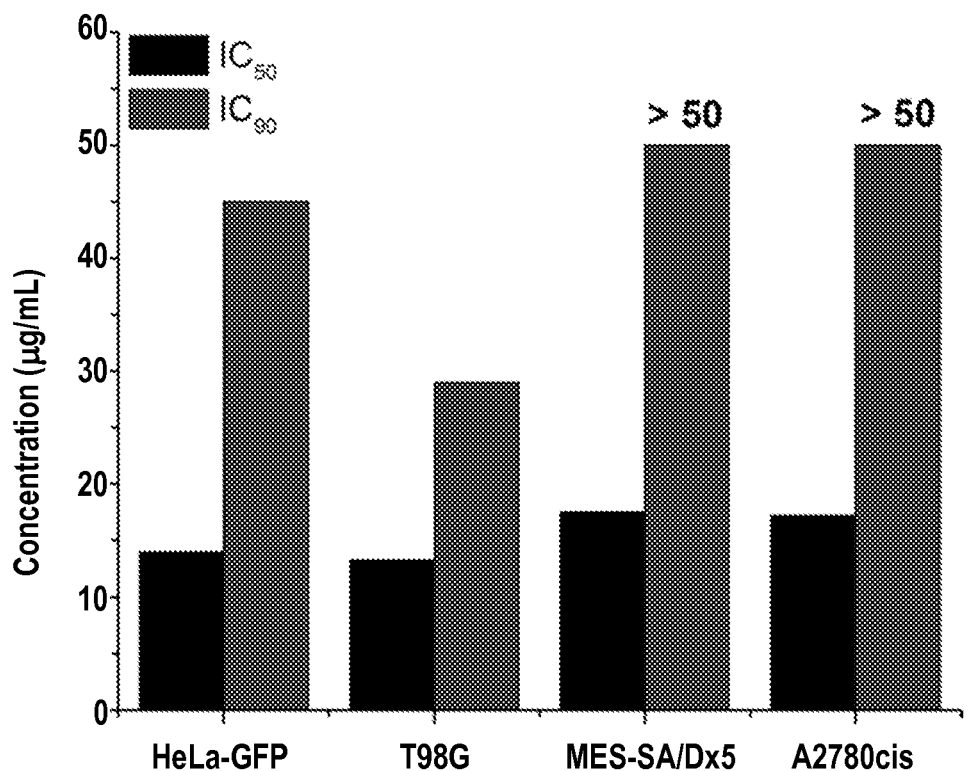
FIG. 16 is a graph showing $IC_{50}$ and $IC_{90}$ values of MNP_pY against HeLa-GFP, T98G, MES-SA/Dx5, A2780-cis cells at 72 hours. The initial number of cells is $1.0 \times 10^4$/well.

FIG. 16 shows that the use of enzymatic reaction rather than ligand-receptor interaction enables nanoparticles to selectively inhibit cancer cells (e.g., HeLa-GFP) without comprising stromal cells (e.g., HS-5) in co-culture. Specifically, magnetic nanoparticles (10 nm in diameter) were decorated with D-tyrosine phosphate and it was found that these nanoparticles inhibited cancer cells at the $IC_{90}$ of 45 and 29 µg/mL against HeLa-GFP and T98G cells, respectively and $IC_{50}$ of 17 µg/mL against MES-SA/Dx5 cells. These activities are comparable or even higher than nanoparticles loaded with cisplatin (one of most successful chemotherapy agents).

Figure 17:
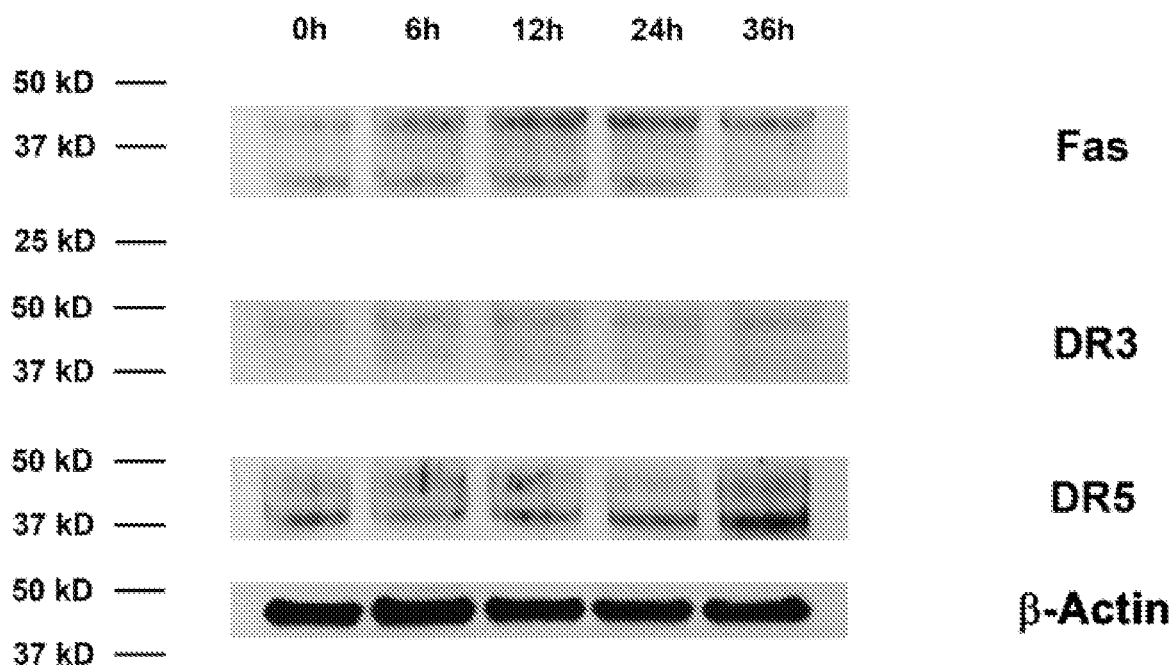
FIG. 17 is an image of a Western blot analysis showing changes in relative amount of cell death receptor proteins over time in HeLa-GFP cells treated by MNP_pY at the concentration of 20 µg/mL.

These studies show that an underexplored generic difference—overexpression of ectophosphatases—between cancer and normal cells enabled the magnetic nanoparticles to adhere selectively on cancer cells upon catalytic dephosphorylation for inhibiting cancer cells via extrinsic cell death pathways (e.g., Fas, DR3, or DR5). See FIG. 17. Without phosphate groups, the nanoparticles are innocuous to cells, which confirms that enzymatic reaction confers the nanoparticles with the cancer-tropic ability.

In conclusion, this work, for the first time, demonstrates the use of enzymatic transformation of magnetic nanoparticles for selectively sorting and inhibition of cancer cells from stromal cells without involving specific ligand-receptor interactions or the use of antibodies. The high capture efficiency of cancer cells from the co-culture demonstrated the expression level of enzymes as a new paradigm for exploring strategies that target cancer cells. This strategy relied on an enzymatic reaction (e.g., catalytic dephosphorylation), but not specific enzyme inhibition, to target cancer cells selectively. The same principle should be useful for developing a relatively inexpensive, simple, and selective method for sampling other biological specimens. By mimicking the essence of biological signaling processes (e.g., kinase/phosphatase enzymatic switch (Lodish et al., *Molecular Cell Biology*; Seventh Edition edition ed.; Freeman, W. H. (2012), which is hereby incorporated by reference in its entirety)), the use of enzymatic transformation to control the formation or state of nanostructures (Zhou et al., *J. Am. Chem. Soc.* 136:2970 (2014); Toledano et al., *J. Am. Chem. Soc.* 128:1070 (2006); Yang et al., *J. Am. Chem. Soc.* 129:266 (2007); Yang et al., *Chem. Commun.* 2424 (2004); Lovell et al., *Angew. Chem. Int. Edit.* 51:2429 (2012); Kim et al., *Angew. Chem. Int. Edit.* 47:8438 (2008); Kim et al., *J. Am. Chem. Soc.* 128:688 (2006); Lee et al., *Nat. Med.* 13:95 (2007); Zhao et al., *J. Am. Chem. Soc.* 135:12940 (2013); Xia et al., *Adv. Mater.* 15:353 (2003); Jin et al., *Nat. Nanotechnol.* 4:571 (2009); Yang et al., *J. Am. Chem. Soc.* 130:5286 (2008); Chien et al., *J. Am. Chem. Soc.* 135:18710 (2013); Ku et al., *J. Am. Chem. Soc.* 133:8392 (2011), which are hereby incorporated by reference in their entirety) ultimately may lead to new approaches for detecting and treating other diseases.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A product comprising a single amino acid residue conjugated to a magnetic particle, wherein the single amino acid residue is not present in a polypeptide or protein, and wherein the single amino acid is selected from the group consisting of phosphoserine, sulfoserine, phosphothreonine, sulfothreonine, phosphohistidine, sulfohydroxyproline, phosphotyrosine, and sulfotyrosine.

2. The product according to claim 1, wherein the magnetic particle is a nanoparticle or microparticle, and the magnetic particle is paramagnetic or superparamagnetic.

3. A product comprising a single, phosphorylated amino acid residue (pAA) conjugated to a magnetic particle—wherein the magnetic particle comprises a polymer conjugated to the single, phosphorylated amino acid residue (pAA), where n is any integer

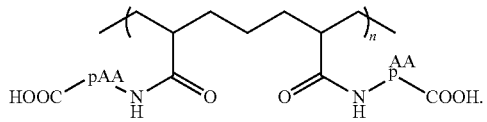

wherein the single, phosphorylated amino acid residue (pAA) is selected from phosphoserine, phosphothreonine, phosphohistidine, and phosphotyrosine.

4. The product according to claim 1, wherein the magnetic particle comprises iron oxide; or wherein the magnetic particle is a core/shell particle, the core comprises cobalt, iron or iron oxide, a cobalt/iron alloy, or a polymer, and the shell comprises graphene, an oxide, gold, silver, platinum, a polymer, or a mixture of a polymer and iron oxide.

5. The product according to claim 1, wherein the product consists of the single amino acid residue conjugated directly to the magnetic particle.

6. A product comprising a polypeptide that includes from 2 to 35 amino acid residues, one of the amino acid residues being conjugated to a magnetic particle and one of the amino acid residues being phosphorylated or sulfated or comprising an ester-moiety linked via peptide bond, wherein the polypeptide further comprises a metalloprotease (MMP) cleavage site and an amino acid sequence selected from the group consisting of:

| Polypeptide | SEQ. ID. NO: |
|---|---|
| X-Gly-Pro-Gln-Gly↓Leu-Ala-Gly-Gln | 1 |
| X-Ala-Pro-Ala-Ala↓Leu-Val-Gly-Ala | 2 |
| X-Ala-Pro-Ala-Gly↓Leu-Lys-Ala-Pro | 3 |
| X-Glu-Pro-Ala-Ser↓Leu-Arg-Ala-Gly | 4 |
| X-Gly-Pro-Gln-Gly↓Leu-Arg-Gly-Arg | 5 |

-continued

| Polypeptide | SEQ. ID. NO: |
|---|---|
| X-Gly-Pro-Ala-Gly↓Leu-Arg-Gly-Pro | 6 |
| X-Gly-Pro-Ala-Gly↓Leu-Gly-Ala-Ala | 7 |
| X-Gly-Pro-Lys-Gly↓Leu-Arg-Gly-Gly | 8 |
| X-Leu-Pro-Leu-Gly↓Leu-Val-Thr-Glu | 9 | wherein X is any aromatic group, aromatic amino acid residue, or hydrophobic amino acid; and ↓ is a MMP cleavage site.

7. The product according to claim 6 wherein the phosphorylated, sulfated, or ester-moiety-modified amino acid residue is separated from the magnetic particle by one or more intervening amino acid residues.

8. The product according to claim 6 wherein the polypeptide further comprises one or more aromatic amino acids that promote hydrogelation in water.

9. A composition comprising an aqueous carrier and a product according to claim 1.

10. A method of separating distinct types of cells in vitro comprising:
exposing a product according to claim 1 to a mixed population of cells including a first cell type that expresses an ectoenzyme that hydrolyzes the phosphate or sulfate group of the product, and a second cell type that lacks an ectoenzyme that hydrolyzes the phosphate or sulfate group of the product whereby the hydrolyzed product labels the first cell type after said exposing;
separating the labeled first cell type from the second cell type.

11. The method according to claim 10, wherein the first cell type is a cancer cell.

12. The method according to claim 10, wherein said separating comprises introducing the exposed, mixed cell population to a magnetic field, wherein the labeled first cell type is retained within the magnetic field and the second cell type is not retained within the magnetic field, thereby separating the first and second cell types.

13. The product according to claim 6, wherein the magnetic particle is a nanoparticle or microparticle, and the magnetic particle is paramagnetic or superparamagnetic.

14. The product according to claim 6, wherein the magnetic particle comprises iron oxide; or wherein the magnetic particle is a core/shell particle, the core comprises cobalt, iron or iron oxide, a cobalt/iron alloy, or a polymer, and the shell comprises graphene, an oxide, gold, silver, platinum, a polymer, or a mixture of a polymer and iron oxide.

15. A composition comprising an aqueous carrier and a product according to claim 6.

* * * * *